(12) United States Patent
Bissantz et al.

(10) Patent No.: US 8,143,281 B2
(45) Date of Patent: *Mar. 27, 2012

(54) INDOLES

(75) Inventors: Caterina Bissantz, Village-Neuf (FR); Christophe Grundschober, Rodersdorf (CH); Raffaello Masciadri, Basel (CH); Hasane Ratni, Habsheim (FR); Mark Rogers-Evans, Oberwil BL (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1120 days.

This patent is subject to a terminal disclaimer.

(21) Appl. No.: 11/959,545

(22) Filed: Dec. 19, 2007

(65) Prior Publication Data

US 2008/0161316 A1  Jul. 3, 2008

(30) Foreign Application Priority Data

Dec. 28, 2006 (EP) ..................................... 06127307

(51) Int. Cl.
  *A61K 31/4985* (2006.01)
  *C07D 401/14* (2006.01)
(52) U.S. Cl. ........................ 514/320; 546/198
(58) Field of Classification Search .................. 514/320; 546/198
See application file for complete search history.

(56) References Cited

U.S. PATENT DOCUMENTS

| 5,686,624 | A | 11/1997 | Di Malta et al. |
| 7,799,923 | B2 * | 9/2010 | Bissantz et al. ............... 546/199 |
| 7,803,815 | B2 * | 9/2010 | Bissantz et al. ............... 514/322 |

FOREIGN PATENT DOCUMENTS

| WO | WO 2007/009906 | 1/2007 |
| WO | 2007/014851 | 2/2007 |
| WO | 2008/068184 | 6/2008 |

OTHER PUBLICATIONS

Bottcher et al. "Preparation of benzyl . . . " CA 130:81409 (1999).*
Ebner et al., (2002), Eur. J. Neurosci. vol. 15 pp. 384-388.
Bielsky et al., (2004), Neuropsychopharmacology, vol. 29 pp. 483-493.
Liebsch et al., (1995), Regulatory Peptides vol. 59 pp. 229-239.
Michelini et al., (1999), Annals NY Acad. Sci. vol. 897 pp. 198-211.
Van Kerckhoven et al., (2002) Eur. J. Pharmacol. vol. 449 pp. 135-141.
Swain et al., J. Med. Chem., vol. 34 p. 140-151 (1991).
Delgado, et al., J. Org. Chem., vol. 10, p. 2862-2866 (1993).
Serradeil-Le Gal et al, *Elsevier*, 139 (2002) 197-210 XP001205440.
Chilean Office Action for Corresponding Appl. 3831-2007 dated Nov. 14, 2010.

* cited by examiner

*Primary Examiner* — Celia Chang
(74) *Attorney, Agent, or Firm* — George W. Johnston; Patricia S. Rocha-Tramaloni; Kimberly J. Prior

(57) ABSTRACT

The present invention is concerned with novel indol-3-yl-carbonyl-piperidine-benzopyrrolone, -benzoxazolone and -benzotriazole derivatives as V1a receptor antagonists, their manufacture, pharmaceutical compositions containing them and their use for the treatment of anxiety and depressive disorders and other diseases. In particular, the present invention is concerned with compounds of formula (I)

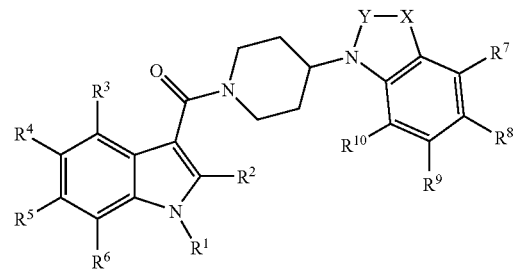

wherein X, Y and $R^1$ to $R^{10}$ are as described in the specification.

18 Claims, No Drawings

INDOLES

PRIORITY TO RELATED APPLICATION(S)

This application claims the benefit of European Patent Application No. 06127307.4, filed Dec. 28, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." Eur J Neurosci 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." Neuropsychopharmacology). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." Regul Pept 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." Ann N Y Acad Sci 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." Eur J Pharmacol 449(1-2): 135-41).

SUMMARY OF THE INVENTION

The present invention provides novel indol-3-yl-carbonyl-piperidine-benzopyrrolone, -benzoxazolone and -benzotriazole derivatives as V1a receptor antagonists, their manufacture, pharmaceutical compositions containing them and their use for the treatment of anxiety and depressive disorders and other diseases.

In particular, the present invention provides compounds of formula (I)

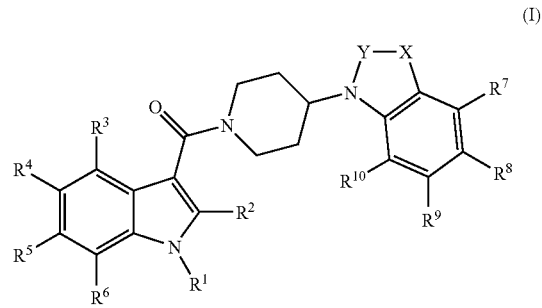

wherein
X is $CH_2$, and Y is $C=O$,
X is O, and Y is $C=O$, or
X—Y is $N=N$;
$R^1$ is H,
  $C_{1-12}$-alkyl, optionally substituted with CN or OH,
  $C_{1-6}$-haloalkyl,
  $C_{2-12}$-alkenyl,
  —$(CR^iR^{ii})_m$—$R^a$,
    wherein $R^i$ and $R^{ii}$ are independently from each other H, methyl, or ethyl;
    wherein m is from 0 to 4;
    wherein $R^a$ is
      phenyl, 5- to 6-membered heteroaryl, 3- to 7-membered heterocycloalkyl
        or 3 to 7-membered cycloalkyl,
          which are optionally substituted with one or more A, or
      —$NR^bR^c$, wherein $R^b$ and $R^c$ are each independently
        hydrogen,
        hydroxy,
        $C_{1-6}$-alkyl,
        —$S(O)_2$—$C_{1-6}$-alkyl, or
        —$C(O)$—$C_{1-6}$-alkyl,
  —$(CR^{iii}R^{iv})_n$—$C(O)R^d$,
    wherein $R^{iii}$ and $R^{iv}$ are each independently H, methyl, or ethyl;
    wherein n is from 0 to 4;
    wherein $R^d$ is
      $C_{1-6}$-alkoxy,
      —$NR^eR^f$, wherein $R^e$ and $R^f$ are each independently
        hydrogen,
        $C_{1-6}$-alkyl, or
        —$(C_{2-6}$-alkylene)-$NR^gR^h$; wherein $R^g$ and $R^h$ are each independently hydrogen, $C_{1-6}$-alkyl, or
          —$C(O)O$—$C_{1-6}$-alkyl, or
      phenyl, 5- to 6-membered heteroaryl, 3- to 7-membered heterocycloalkyl
        or 3 to 7-membered cycloalkyl,
          which are optionally substituted with one or more A,
      —$S(O)_2$-phenyl, wherein phenyl is optionally substituted with one or more halo, $C_{1-6}$-haloalkyl, $C_{1-6}$-alkyl, $C_{1-6}$-alkoxy, $C_{1-6}$-haloalkoxy, nitro, hydroxy or cyano;
      —$S(O)_2$—$C_{1-6}$-alkyl,
      —$S(O)_2N(C_{1-6}$-alkyl)$_2$, or
      —$S(O)_2NH(C_{1-6}$-alkyl);
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$S(O)_{0-2}$ $C_{1-6}$-alkyl, nitro, hydroxy, cyano, —$(C_{1-6}$-alkylene)-O—

$C_{1-6}$-alkyl, —($C_{1-6}$-alkylene)-O—$C_{1-6}$-haloalkyl, —($C_{1-6}$- alkylene)-OR''', —C(O)O$C_{1-6}$-alkyl, —C(O)$C_{1-6}$- alkyl, —C(O)OR''', —C(O)R''', —C(O)NR'R'', —S(O)$_2$ NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, or —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy,
$R^2$ is hydrogen,
$C_{1-6}$-alkyl, or
—C(O)R'', wherein R'' is
$C_{1-6}$-alkyl,
3 to 7-membered heterocycloalkyl, optionally substituted with one, two or three $C_{1-6}$-alkyl, —C(O)O—$C_{1-6}$-alkyl, or —S(O)$_2$—$C_{1-6}$-alkyl, or
NR$^j$R$^k$, wherein R$^j$ and R$^k$ are each independently
hydrogen,
$C_{1-6}$-alkyl, or
—($C_{2-6}$-alkylene)-NR$^l$R$^m$; wherein R$^l$ and R$^m$ are each independently hydrogen, $C_{1-6}$-alkyl, or —C(O)O—$C_{1-6}$-alkyl; or
$R^1$ together with $R^2$ forms a 5- to 6-membered heterocycloalkyl moiety fused to the indole core, bearing one or two ring heteroatoms selected from N, S and O, and being optionally substituted by one or more A;
$R^3$, $R^4$, $R^5$, $R^6$ are each independently hydrogen, halo, $C_{1-6}$-alkyl, halo-$C_{1-6}$-alkyl, $C_{1-6}$-alkoxy or $C_{1-6}$-haloalkoxy;
$R^7$, $R^8$, $R^9$, $R^{10}$ are each independently hydrogen, halo, $C_{1-6}$-alkyl, halo-$C_{1-6}$-alkyl, $C_{1-6}$-alkoxy or $C_{1-6}$-haloalkoxy;
or a pharmaceutically acceptable salt thereof,
with the proviso that compounds wherein $R^1$, $R^2$, $R^3$, $R^4$, $R^5$ and $R^6$ are all simultaneously hydrogen are excluded.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor. Such antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

In the present description, the term "alkyl," alone or in combination with other groups, refers to a branched or straight-chain monovalent saturated hydrocarbon radical.

The term "$C_{1-6}$-alkyl" denotes a saturated straight- or branched-chain hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of $C_{1-6}$-alkyl is $C_{1-4}$-alkyl, i.e. with 1-4 carbon atoms.

In the present invention, the term "alkylene" refers to a linear or branched saturated divalent hydrocarbon radical. In particular, "$C_{1-6}$-alkylene", means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, 1-methyl-ethylene, 2-methyl-ethylene and the like.

In the present description, the terms "alkoxy" and "$C_{1-6}$-alkoxy" refer to the group R'—O—, wherein R' is alkyl or $C_{1-6}$-alkyl as defined above. Examples of alkoxy groups are methoxy, ethoxy, n-propoxy, isopropoxy, n-butoxy, tert-butoxy, sec-butoxy and the like. A preferred sub-group of $C_{1-6}$-alkoxy, and still more preferred alkoxy groups are methoxy and/or ethoxy.

In the present description, the terms "thioalkyl" and "$C_{1-6}$-thioalkyl" refer to the group R'—S—, wherein R' is alkyl or $C_{1-6}$-alkyl as defined above. The term "—S(O)$_{0-2}$$C_{1-6}$-alkyl" hence refers to the residues —S—$C_{1-6}$-alkyl, —S(O)—$C_{1-6}$-alkyl, and —S(O)$_2$—$C_{1-6}$-alkyl wherein $C_{1-6}$-alkyl is as defined above.

The term "$C_{1-6}$-alkyl substituted by OH" is synonymous with "$C_{1-6}$-hydroxyalkyl" or "hydroxyl-$C_{1-6}$-alkyl" and means a $C_{1-6}$-alkyl group as defined above wherein at least one of the hydrogen atoms of the alkyl group is replaced by a hydroxy group.

The term "$C_{1-6}$-alkyl substituted by CN" is synonymous with "$C_{1-6}$-cyanoalkyl" or "cyano-$C_{1-6}$-alkyl" and means a $C_{1-6}$-alkyl group as defined above wherein at least one of the hydrogen atoms of the alkyl group is replaced by a CN group.

The terms "halo" and "halogen" refer to fluorine (F), chlorine (Cl), bromine (Br) and iodine (I) with fluorine, chlorine and bromine being preferred.

The term "$C_{1-6}$-haloalkyl" is synonymous with "halo-$C_{1-6}$-alkyl" or "$C_{1-6}$-alkyl substituted by halo" and means a $C_{1-6}$-alkyl group as defined above wherein at least one of the hydrogen atoms of the alkyl group is replaced by a halogen atom, preferably fluoro or chloro, most preferably fluoro. Examples of $C_{1-6}$-haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred $C_{1-6}$-haloalkyl groups are difluoro- or trifluoro-methyl or -ethyl.

The term "$C_{1-6}$-haloalkoxy" is synonymous with "halo-$C_{1-6}$-alkoxy" or "$C_{1-6}$-alkoxy substituted by halo" and means a $C_{1-6}$-alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

The term "$C_{2-12}$-alkenyl," alone or in combination, denotes a straight-chain or branched hydrocarbon residue of 2 to 12 carbon atoms comprising at least one double bond. A preferred sub-group of $C_{2-12}$-alkenyl is $C_{2-6}$-alkyenyl. Examples of the preferred alkenyl groups are ethenyl, propen-1-yl, propen-2-yl(allyl), buten-1-yl, buten-2-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "5 or 6 membered heteroaryl" means a monovalent aromatic ring of 5 or 6 ring atoms as ring members containing one, two, three or four ring heteroatoms selected from N, O, and S, the rest being carbon atoms, whereby one, two or three heteroatoms are preferred, and one or two heteroatoms are even more preferred. Examples of heteroaryl moieties include, but are not limited to pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. 5 or 6-membered heteroaryl are optionally substituted with one or more substituents. These optional substituents include halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}$$C_{1-6}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)O$C_{1-6}$-alkyl, —C(O)$C_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, —(CH$_2$)$_x$—R''', wherein x is from 0 to 4, R' and R'' are each independently H or $C_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy. Preferred substituents are halo, $C_{1-6}$-haloalkyl, $C_{1-6}$-alkyl, $C_{1-6}$-alkoxy, $C_{1-6}$-haloalkoxy, cyano, —CH$_2$CN, —CH$_2$OCH$_3$, —S(O)$_2$—$C_{1-6}$-alkyl, $C_{1-6}$-hydroxyalkyl, —NR'C(O)—$C_{1-4}$-alkyl, —C(O)N($C_{1-4}$-alkyl)$_2$, —C(O)NH($C_{1-4}$-alkyl), —S(O)$_2$N($C_{1-4}$-alkyl)$_2$, or —S(O)$_2$NH($C_{1-4}$-alkyl), or those substitutents as specifically indicated herein.

The term "heterocycloalkyl" means a monovalent saturated ring, consisting of one ring of 3 to 7, preferably from 4 to 6 atoms as ring members, including one, two, three or four heteroatoms chosen from nitrogen, oxygen or sulfur, the rest being carbon atoms, whereby one, two or three heteroatoms are preferred, and one or two heteroatoms are even more preferred. It is understood that the number of heteroatoms depends on the ring size, i.e. 3 and 4-membered heterocycloalkyl preferably contain one heteroatom, 5 to 7-membered heterocycloalkyl preferably contain one, two or three heteroatoms, and even more preferably one or two heteroatoms. Examples of heterocyclic moieties include, but are not limited to, oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl, each of which is optionally substituted as described herein. 3 to 7-membered heterocycloalkyl are optionally substituted with one or more substituents. These optional substitutents include halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}$$C_{1-6}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)O$C_{1-6}$-alkyl, —C(O)$C_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, —(CH$_2$)$_x$—R''', wherein x is from 0 to 4, R' and R'' are each independently H or $C_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy. Preferred substituents are halo, $C_{1-6}$-haloalkyl, $C_{1-6}$-alkyl, $C_{1-6}$-alkoxy, $C_{1-6}$-haloalkoxy, cyano, —CH$_2$CN, —CH$_2$OCH$_3$, —S(O)$_2$—$C_{1-6}$-alkyl, $C_{1-6}$-hydroxyalkyl, —NR'C(O)—$C_{1-4}$-alkyl, —C(O)N($C_{1-4}$-alkyl)$_2$, —C(O)NH($C_{1-4}$-alkyl), —S(O)$_2$N($C_{1-4}$-alkyl)$_2$, or —S(O)$_2$NH($C_{1-4}$-alkyl), or those substitutents as specifically indicated herein.

The term "one or more substituents" indicates that in principle every position in the aryl (in particular phenyl), heteroaryl, heterocycloalkyl and cycloalkyl residue may bear such a substituent. The pentafluorophenyl residue may be mentioned as a preferred example. However, in 5 to 6-membered aromatic rings, one, two, or three substituents are preferred. In 5 to 6-membered saturated rings, one, two three or four substituents are preferred. In 3 to 4-membered rings, one or two substituents are preferred.

The term "heterocycle" in the definition "R' and R'', together with the nitrogen to which they are bound form a five- or six-membered heterocycle comprising one or two heteroatoms selected from the group of nitrogen, oxygen and sulfur" means either heterocycloalkyl or partially unsaturated heterocycloalkyl (synonymous with heterocycloalkenyl), which may optionally be substituted with one, two or three substituents selected from halo, $C_{1-6}$-haloalkyl, $C_{1-6}$-alkyl, $C_{1-6}$-alkoxy, $C_{1-6}$-haloalkoxy, nitro, and cyano. Preferred heterocycles are piperazine, N-methylpiperazine, morpholin, piperidine and pyrrolidine.

The term "$C_{3-7}$-cycloalkyl" denotes a monovalent or divalent saturated carbocyclic moiety consisting of a monocyclic ring containing from 3 to 7 ring carbon atoms. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" or "pharmaceutically acceptable salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The invention further comprises individual optical isomers of the compounds described herein as well as racemic and non-racemic mixtures thereof.

In detail, the present invention relates to compounds of the general formula (I)

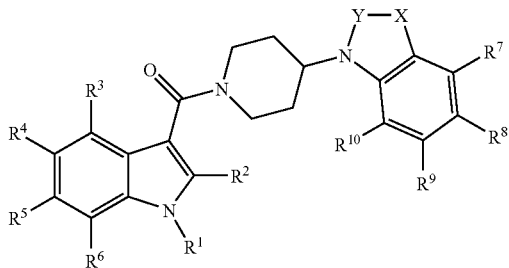

wherein
X is CH$_2$, and Y is C=O,
X is O, and Y is C=O, or
X—Y is N=N;
R$^1$ is H,
  C$_{1-12}$-alkyl, optionally substituted with CN or OH,
  C$_{1-6}$-haloalkyl,
  C$_{2-12}$-alkenyl,
  —(CR$^i$R$^{ii}$)$_m$—R$^a$,
    wherein R$^i$ and R$^{ii}$ are independently from each other H, methyl, or ethyl;
    wherein m is from 0 to 4;
    wherein R$^a$ is
      phenyl, 5- to 6-membered heteroaryl, 3- to 7-membered heterocycloalkyl
      or 3 to 7-membered cycloalkyl,
        which are optionally substituted with one or more A, or
      —NR$^b$R$^c$, wherein R$^b$ and R$^c$ are each independently
        hydrogen,
        hydroxy,
        C$_{1-6}$-alkyl,
        —S(O)$_2$—C$_{1-6}$-alkyl, or
        —C(O)—C$_{1-6}$-alkyl,
  —(CR$^{iii}$R$^{iv}$)$_n$—C(O)R$^d$,
    wherein R$^{iii}$ and R$^{iv}$ are independently from each other H, methyl, or ethyl;
    wherein n is from 0 to 4;
    wherein R$^d$ is
      C$_{1-6}$-alkoxy,
      —NR$^e$R$^f$, wherein R$^e$ and R$^f$ are each independently
        hydrogen,
        C$_{1-6}$-alkyl, or
        —(C$_{2-6}$-alkylene)NR$^g$R$^h$; wherein R$^g$ and R$^h$ are each independently
          hydrogen, C$_{1-6}$-alkyl, or —C(O)O—C$_{1-6}$-alkyl, or
      phenyl, 5- to 6-membered heteroaryl, 3- to 7-membered heterocycloalkyl
      or 3 to 7-membered cycloalkyl,
        which are optionally substituted with one or more A,
  —S(O)$_2$-phenyl, wherein phenyl is optionally substituted with one or more halo, C$_{1-6}$-haloalkyl, C$_{1-6}$-alkyl, C$_{1-6}$-alkoxy, C$_{1-6}$-haloalkoxy, nitro, hydroxy or cyano;
  —S(O)$_2$—C$_{1-6}$-alkyl,
  —S(O)$_2$N(C$_{1-6}$-alkyl)$_2$, or
  —S(O)$_2$NH(C$_{1-6}$-alkyl);
A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$C$_{1-6}$-alkyl, nitro, hydroxy, cyano,
  —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)C$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, or —(CH$_2$)$_x$—R''',
  wherein x is from 0 to 4,
  R' and R'' are each independently H or C$_{1-6}$-alkyl, or
  R' and R'' together with the nitrogen to which they are bound form a 5 or 6-membered heterocycle comprising one or two heteroatoms selected from N, O and S, and
  R''' is phenyl or 5- to 6-membered heteroaryl, optionally substituted with one, two, or three halo, C$_{1-6}$-haloalkyl, C$_{1-6}$-alkyl, or C$_{1-6}$-alkoxy,
R$^2$ is hydrogen,
  C$_{1-6}$-alkyl, or
  —C(O)R$^n$, wherein R$^n$ is
    C$_{1-6}$-alkyl, or
    3 to 7-membered heterocycloalkyl, optionally substituted with one, two or three C$_{1-6}$-alkyl, —C(O)O—C$_{1-6}$-alkyl, or —S(O)$_2$—C$_{1-6}$-alkyl,
  NR$^j$R$^k$, wherein R$^j$ and R$^k$ are each independently
    hydrogen,
    C$_{1-6}$-alkyl, or
    —(C$_{2-6}$-alkylene)-NR$^l$R$^m$; wherein R$^l$ and R$^m$ are each independently hydrogen, C$_{1-6}$-alkyl, or —C(O)O—C$_{1-6}$-alkyl; or
R$^1$ together with R$^2$ forms a 5- to 6-membered heterocycloalkyl moiety fused to the indole core, bearing one or two ring heteroatoms selected from N, S and O, and being optionally substituted by one or more A;
R$^3$, R$^4$, R$^5$, R$^6$ are each independently hydrogen, halo, C$_{1-6}$-alkyl, halo-C$_{1-6}$-alkyl, C$_{1-6}$-alkoxy or C$_{1-6}$-haloalkoxy;
R$^7$, R$^8$, R$^9$, R$^{10}$ are each independently hydrogen, halo, C$_{1-6}$-alkyl, halo-C$_{1-6}$-alkyl, C$_{1-6}$-alkoxy or C$_{1-6}$-haloalkoxy;
or a pharmaceutically acceptable salt thereof,
with the proviso that compounds wherein R$^1$, R$^2$, R$^3$, R$^4$, R$^5$ and R$^6$ are all simultaneously hydrogen are excluded.

In the following, certain embodiments of the invention are disclosed, whereby the combination of these embodiments with each other is also encompassed by present invention.

In certain embodiments of the invention, R$^1$ is hydrogen. However, not all residues R$^1$ to R$^6$ shall simultaneously be hydrogen.

In certain embodiments of the invention, R$^1$ is C$_{1-12}$-alkyl, optionally substituted with CN or OH; or R$^1$ is C$_{2-12}$-alkyl, optionally substituted with CN or OH. Preferably, R$^1$ is C$_{1-6}$-alkyl, optionally substituted with CN or OH; or R$^1$ is C$_{2-6}$-alkyl, optionally substituted with CN or OH.

In certain embodiments of the invention, R$^1$ is C$_{1-6}$-haloalkyl or C$_{2-12}$-alkenyl. In case R$^1$ is alkenyl, C$_{2-6}$-alkenyl is preferred.

In certain embodiments of the invention,
R$^1$ is —(CR$^i$R$^{ii}$)$_m$—R$^a$,
  wherein R$^i$ and R$^{ii}$ are independently from each other H, methyl, or ethyl;
  wherein m is from 0 to 4;
  wherein R$^a$ is
    phenyl, 5- to 6-membered heteroaryl, 3- to 7-membered heterocycloalkyl
    or 3 to 7-membered cycloalkyl,
      which are optionally substituted with one or more halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$C$_{1-6}$-alkyl, nitro, hydroxy, cyano, —($C_{1-6}$-alkylene)-O—$C_{1-6}$-alkyl, —($C_{1-6}$- alkylene)-O—$C_{1-6}$-haloalkyl, —($C_{1-6}$-alkylene)-OR''', —C(O)O$C_{1-6}$-alkyl, —C(O)$C_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, or —(CH$_2$)$_x$—R''', wherein x is from 0 to 4, R' and R'' are each independently H or $C_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy, —NR$^b$R$^c$, wherein R$^b$ and R$^c$ are each independently hydrogen, hydroxy, $C_{1-6}$-alkyl, —S(O)$_2$—$C_{1-6}$-alkyl, or —C(O)—$C_{1-6}$-alkyl.

In —(CR$^i$R$^{ii}$)$_m$—R$^a$, preferably, all R$^i$ and R$^{ii}$ are hydrogen, or one R$^i$ is methyl and the other R$^i$ and R$^{ii}$ are hydrogen. The following linkers —(CR$^i$R$^{ii}$)$_m$— are preferred: —CH$_2$—, —CH(CH$_3$)—, —CH$_2$CH$_2$—, —CH$_2$CH$_2$CH$_2$—, —CH(CH$_3$)CH$_2$—, —CH$_2$CH(CH$_3$)—, —CH(CH$_3$)CH$_2$CH$_2$—, —CH$_2$CH(CH$_3$)CH$_2$—, or —CH$_2$CH$_2$CH(CH$_3$)—.

The variable m in —(CR$^i$R$^{ii}$)$_m$—R$^a$ is 0, 1, 2, 3 or 4. In case R$^a$ is —NR$^b$R$^c$, m is preferably 1, 2, 3 or 4.

When R$^a$ in —(CR$^i$R$^{ii}$)$_m$—R$^a$ is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. In case m is 0, pyridinyl is preferred, in case m is 1, 2, 3 or 4, pyridinyl, pyrimidinyl, pyrazinyl, pyridazinyl, imidazolyl, pyrazolyl, oxazolyl, isoxazolyl, or thiazolyl are preferred. All these residues are optionally substituted as described herein.

When R$^a$ in —(CR$^i$R$^{ii}$)$_m$—R$^a$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. When R$^a$ is 3- to 7-membered heterocycloalkyl, oxiranyl, oxetanyl, pyrrolidinyl, piperidinyl, piperazidinyl, morpholinyl, or tetrahydropyranyl are preferred. All these residues are optionally substituted as described herein.

When R''' is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Pyridinyl, pyrimidinyl, imidazolyl, pyrazolyl, oxazolyl, isoxazolyl, or thiazolyl are preferred.

In certain embodiments of the invention,
R$^1$ is —(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is $C_{1-6}$-alkoxy, —NR$^e$R$^f$, wherein R$^e$ and R$^f$ are each independently hydrogen, $C_{1-6}$-alkyl, or —($C_{2-6}$-alkylene)NR$^g$R$^h$; wherein R$^g$ and R$^h$ are each independently hydrogen, $C_{1-6}$-alkyl, or —C(O)O—$C_{1-6}$-alkyl, or phenyl, 5- to 6-membered heteroaryl, 3- to 7-membered heterocycloalkyl or 3 to 7-membered cycloalkyl, which are optionally substituted with one or more halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}$$C_{1-6}$-alkyl, nitro, hydroxy, cyano, —($C_{1-6}$-alkylene)-O—$C_{1-6}$-alkyl, —($C_{1-6}$- alkylene)-O—$C_{1-6}$-haloalkyl, —($C_{1-6}$-alkylene)-OR''', —C(O)O$C_{1-6}$-alkyl, —C(O)$C_{1-6}$- alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, or —(CH$_2$)$_x$—R''', wherein x is from 0 to 4, R' and R'' are each independently H or $C_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy.

In —(CR$^{iii}$R$^{iv}$)$_n$—C(O)R$^d$, preferably, all R$^{iii}$ and R$^{iv}$ are hydrogen, or one R$^{iii}$ is methyl and the other R$^{iii}$ and R$^{iv}$ are hydrogen. The following linkers —(CR$^i$R$^{ii}$)$_n$— are preferred: —CH$_2$—, —CH(CH$_3$)—, —CH$_2$CH$_2$—, —CH$_2$CH$_2$CH$_2$—, —CH(CH$_3$)CH$_2$—, —CH$_2$CH(CH$_3$)—, —CH(CH$_3$)CH$_2$CH$_2$—, —CH$_2$CH(CH$_3$)CH$_2$—, or —CH$_2$CH$_2$CH(CH$_3$)—.

The variable n in —(CR$^{iii}$R$^{iv}$)$_n$—C(O)R$^d$ is 0, 1, 2, 3 or 4.

When R$^d$ in —(CR$^{iii}$R$^{iv}$)$_n$—C(O)R$^d$ is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. When R$^d$ is 5- to 6-membered heteroaryl, optionally substituted pyridinyl is preferred. All these residues are optionally substituted as described herein.

When R$^d$ in —(CR$^{iii}$R$^{iv}$)$_n$—C(O)R$^d$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. When R$^d$ is 3- to 7-membered heterocycloalkyl, optionally substituted piperidinyl, piperazidinyl, or morpholinyl are preferred. All these residues are optionally substituted as described herein.

When R''' is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Pyridinyl, pyrimidinyl, imidazolyl, pyrazolyl, oxazolyl, isoxazolyl, or thiazolyl are preferred.

In certain embodiments of the invention, $R^1$ is —S(O)$_2$-phenyl, wherein phenyl is optionally substituted with one or more halo, $C_{1-6}$-haloalkyl, $C_{1-6}$-alkyl, $C_{1-6}$-alkoxy, $C_{1-6}$-haloalkoxy, nitro, hydroxy or cyano. Halo, CF$_3$, $C_{1-4}$-alkyl, $C_{1-6}$-alkoxy, OCF$_3$ and cyano are preferred substitutents.

In certain embodiments of the invention, $R^1$ is —S(O)$_2$—$C_{1-6}$-alkyl, —S(O)$_2$N($C_{1-6}$-alkyl)$_2$, or —S(O)$_2$NH($C_{1-6}$-alkyl).

It is understood that all the above residues $R^1$ are encompassed by present invention in all their possible combinations. Some examples are given below.

In certain embodiments of the invention,

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}$ $C_{1-6}$-alkyl, nitro, cyano, —(C$_{1-6}$-alkylene)-O—C$_{1-6}$-alkyl, —(C$_{1-6}$-alkylene)-OR''', —C(O)OC$_{1-6}$-alkyl, —C(O) NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$ —C$_{1-6}$-alkyl, —(CH$_2$)$_x$—C$_{3-6}$-cycloalkyl, or —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl, optionally substituted with one, two, or three halo, $C_{1-6}$-haloalkyl, $C_{1-6}$-alkyl, or $C_{1-6}$-alkoxy.

In certain embodiments of formula (I) of the invention,

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, $C_{1-6}$-thioalkyl, —S(O)$_2$—$C_{1-6}$-alkyl, cyano, —CH$_2$OCH$_3$, —C(O)O—C$_{1-6}$-alkyl, —C(O)NR'R'', —S(O)$_2$NR'R'', —NR'C(O)—C$_{1-6}$-alkyl, —NR'S(O)$_2$—C$_{1-6}$-alkyl, benzyl, or phenyl
wherein R' and R'' are each independently H or $C_{1-6}$-alkyl.

In certain embodiments of formula (I) of the invention, $R^1$ is H, $C_{2-6}$-alkyl, optionally substituted with CN or OH,
$C_{1-6}$-haloalkyl,
—(CR$^i$R$^{ii}$)$_m$—R$^a$,
wherein R$^i$ and R$^{ii}$ are independently from each other H, methyl, or ethyl;
wherein m is from 0 to 4;
wherein R$^a$ is
phenyl, 5- to 6-membered heteroaryl, 3- to 7-membered heterocycloalkyl
or 3 to 7-membered cycloalkyl,
which are optionally substituted with one or more A, or
—NR$^b$R$^c$, wherein R$^b$ and R$^c$ are each independently hydrogen, $C_{1-6}$-alkyl, —S(O)$_2$—$C_{1-6}$-alkyl, or —C(O)—$C_{1-6}$-alkyl,
—(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is
$C_{1-6}$-alkoxy,
—NR$^e$R$^f$, wherein R$^e$ and R$^f$ are each independently hydrogen,
$C_{1-6}$-alkyl, or
—(C$_{2-6}$-alkylene)NR$^g$R$^h$; wherein R$^g$ and R$^h$ are each independently
hydrogen, $C_{1-6}$-alkyl, or —C(O)O—$C_{1-6}$-alkyl, or
phenyl, 5- to 6-membered heteroaryl, 3- to 7-membered heterocycloalkyl
or 3 to 7-membered cycloalkyl,
which are optionally substituted with one or more A,
—S(O)$_2$—$C_{1-6}$-alkyl,
—S(O)$_2$N($C_{1-6}$-alkyl)$_2$, or
—S(O)$_2$NH($C_{1-6}$-alkyl);

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}$ $C_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)C$_{1-6}$-alkyl, —C(O)OR''', —C(O)R''', —C(O)NR'R'', —S(O)$_2$ NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, or —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy.

In certain embodiments of formula (I) of the invention, $R^1$ is H, $C_{2-6}$-alkyl, optionally substituted with CN or OH,
$C_{1-6}$-haloalkyl,
(CR$^i$R$^{ii}$)$_m$—R$^a$,
wherein R$^i$ and R$^{ii}$ are independently from each other H, methyl, or ethyl;
wherein m is from 1 to 4;
wherein R$^a$ is
phenyl, 5- to 6-membered heteroaryl, 3- to 7-membered heterocycloalkyl
or 3 to 7-membered cycloalkyl,
which are optionally substituted with one or more A, or
—NR$^b$R$^c$, wherein R$^b$ and R$^c$ are each independently hydrogen, $C_{1-6}$-alkyl, —S(O)$_2$—$C_{1-6}$-alkyl, or —C(O)—$C_{1-6}$-alkyl,
—(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is
$C_{1-6}$-alkoxy,
—NR$^e$R$^f$, wherein R$^e$ and R$^f$ are each independently hydrogen,
$C_{1-6}$-alkyl, or
—(C$_{2-6}$-alkylene)NR$^g$R$^h$; wherein R$^g$ and R$^h$ are each independently
hydrogen, $C_{1-6}$-alkyl, or —C(O)O—$C_{1-6}$-alkyl, or
phenyl, 5- to 6-membered heteroaryl, 3- to 7-membered heterocycloalkyl
or 3 to 7-membered cycloalkyl,
which are optionally substituted with one or more A, —S(O)$_2$—C$_{1-6}$-alkyl,
—S(O)$_2$N(C$_{1-6}$-alkyl)$_2$, or
—S(O)$_2$NH(C$_{1-6}$-alkyl);

A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$C$_{1-6}$-alkyl, nitro, cyano, —(C$_{1-6}$-alkylene)-O—C$_{1-6}$-alkyl, —(C$_{1-6}$-alkylene)-OR''', —C(O)OC$_{1-6}$-alkyl, —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, or —(CH$_2$)$_x$—R''', wherein x is from 0 to 4, R' and R'' are each independently H or C$_{1-6}$-alkyl, or R' and R'' together with the nitrogen to which they are bound form a 5 or 6-membered heterocycle comprising one or two heteroatoms selected from N, O and S, and R''' is phenyl, optionally substituted with one, two, or three halo, C$_{1-6}$-haloalkyl, C$_{1-6}$-alkyl, or C$_{1-6}$-alkoxy.

Preferably, A is selected from halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, C$_{1-6}$-thioalkyl, —S(O)$_2$—C$_{1-6}$-alkyl, cyano, —CH$_2$OCH$_3$, —C(O)O—C$_{1-6}$-alkyl, —C(O)NR'R'', —S(O)$_2$NR'R'', —NR'C(O)—C$_{1-6}$-alkyl, —NR'S(O)$_2$—C$_{1-6}$-alkyl, benzyl, and phenyl wherein R' and R'' are each independently H or C$_{1-6}$-alkyl.

In certain embodiments of formula (I) of the invention, R$^1$ together with R$^2$ forms a 5- to 6-membered heterocycloalkyl moiety fused to the indole core, bearing one or two ring heteroatoms selected from N, S and O, and being optionally substituted by one or more A. Thereby, A is as defined above. Preferably, the optional substituents are selected from C$_{1-6}$-alkyl, halo, C$_{1-6}$-haloalkyl, C$_{1-6}$-alkoxy and C$_{1-6}$-haloalkoxy. Preferably, it is one optional substituent.

In certain embodiments of formula (I) of the invention, R$^1$ is H,

—(CR$^i$R$^{ii}$)$_m$—R$^a$, wherein R$^i$ and R$^{ii}$ are H, and m is 1 or 2;

wherein R$^a$ is phenyl, optionally substituted with one or more A, preferably with halo, —NR$^b$R$^c$, wherein R$^b$ and R$^c$ are each independently hydrogen, C$_{1-6}$-alkyl, —S(O)$_2$—C$_{1-6}$-alkyl, or —C(O)—C$_{1-6}$-alkyl, or —(CR$^{iii}$R$^{iv}$)$_n$—C(O)R$^d$, wherein R$^{iii}$ and R$^{iv}$ are H, and n is 1, and R$^d$ is —NR$^e$R$^f$, wherein R$^e$ and R$^f$ are each independently hydrogen or C$_{1-6}$-alkyl, or R$^1$ together with R$^2$ forms a 6-membered hetercycloalkyl moiety fused to the indole core, bearing two nitrogen ring heteroatoms, and being optionally substituted by one or more C$_{1-6}$-alkyl, halo, C$_{1-6}$-haloalkyl, C$_{1-6}$-alkoxy or C$_{1-6}$-haloalkoxy, A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, C$_{1-6}$-thioalkyl, —S(O)$_2$—C$_{1-6}$-alkyl, cyano, —CH$_2$OCH$_3$, —C(O)O—C$_{1-6}$-alkyl, —C(O)NR'R'', —S(O)$_2$NR'R'', —NR'C(O)—C$_{1-6}$-alkyl, —NR'S(O)$_2$—C$_{1-6}$-alkyl, benzyl, or phenyl wherein R' and R'' are each independently H or C$_{1-6}$-alkyl.

When R'' in —C(O)R'' of R$^2$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. When R'' is 3- to 7-membered heterocycloalkyl, piperidinyl, piperazidinyl, or morpholinyl, optionally substituted with one methyl, are preferred.

In certain embodiments of the invention, R$^2$ of the compounds of formula (I) is hydrogen or C$_{1-6}$-alkyl.

In certain embodiments of the invention, R$^1$ together with R$^2$ of formula (I) forms a 5- to 6-membered heterocycloalkyl moiety fused to the indole core, bearing one or two ring heteroatoms selected from N, S and O, and being optionally substituted by one or more A. Preferably, the optional substituents are C$_{1-6}$-alkyl, halo, C$_{1-6}$-haloalkyl, C$_{1-6}$-alkoxy or C$_{1-6}$-haloalkoxy. Preferably, R$^1$ together with R$^2$ of formula (I) forms a 6-membered hetercycloalkyl moiety fused to the indole core, bearing two nitrogen ring heteroatoms, and being optionally substituted by one or more C$_{1-6}$-alkyl, halo, C$_{1-6}$-haloalkyl, C$_{1-6}$-alkoxy or C$_{1-6}$-haloalkoxy.

In certain embodiments of the invention, R$^3$, R$^4$, R$^5$, R$^6$ are each independently hydrogen, halo, C$_{1-6}$-alkyl, C$_{1-6}$-haloalkyl, C$_{1-6}$-alkoxy or C$_{1-6}$-haloalkoxy.

In certain embodiments of the invention, R$^3$ and R$^6$ of formula (I) are hydrogen.

In certain embodiments of the invention, R$^4$ of formula (I) is hydrogen, Cl, F or methyl.

In certain embodiments of the invention, R$^5$ of formula (I) is hydrogen, halo, CF$_3$, methoxy or —OCF$_3$. If R$^5$ is hydrogen, R$^1$ is preferably as defined above, however, with the exclusion of hydrogen. In further embodiments, R$^5$ is halo, CF$_3$, methoxy or —OCF$_3$. In further embodiments, R$^5$ is Cl, F or methoxy; in further embodiments, R$^5$ is Cl.

In certain embodiments of the invention, R$^3$ and R$^6$ are hydrogen, R$^4$ is hydrogen, F, Cl or methyl, and R$^5$ is halo, CF$_3$, methoxy or OCF$_3$.

In certain embodiments of the invention, R$^7$, R$^8$, R$^9$, R$^{10}$ are each independently hydrogen, halo, C$_{1-6}$-alkyl, halo-C$_{1-6}$-alkyl, C$_{1-6}$-alkoxy or C$_{1-6}$-haloalkoxy. Preferably, R$^7$, R$^8$, R$^9$, R$^{10}$ are each hydrogen.

In a certain embodiment the compounds of the invention are those compounds of formula (I-a):

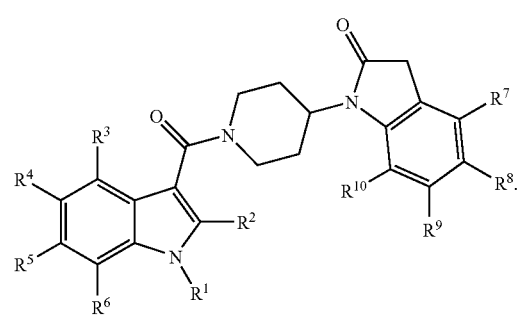

(I-a)

In a certain embodiment the compounds of the invention are those compounds of formula (I-b):

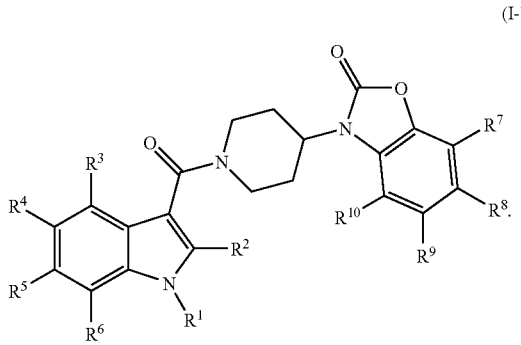

In a certain embodiment the compounds of the invention are those compounds of formula (I-c):

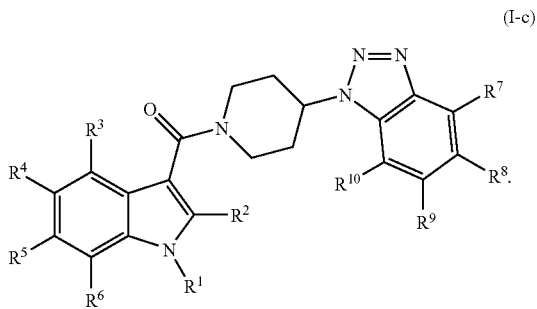

One embodiment of the invention encompasses compounds of formula (I)

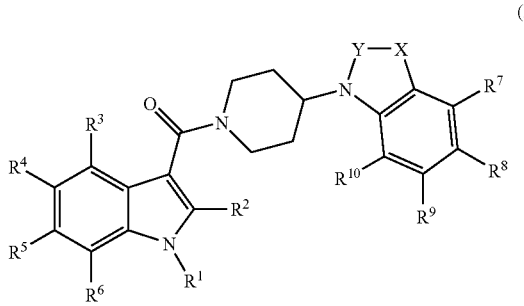

wherein
X is CH$_2$, and Y is C=O,
X is O, and Y is C=O, or
X—Y is N=N;
R$^1$ is H,
  C$_{1-12}$-alkyl, optionally substituted with CN or OH,
  C$_{1-6}$-haloalkyl,
  C$_{2-12}$-alkenyl,
  —(CR$^i$R$^{ii}$)$_m$—R$^a$,
    wherein R$^i$ and R$^{ii}$ are independently from each other H, methyl, or ethyl;
    wherein m is from 0 to 4;
    wherein R$^a$ is
      phenyl, 5- to 6-membered heteroaryl, 3- to 7-membered heterocycloalkyl
      or 3 to 7-membered cycloalkyl,
        which are optionally substituted with one or more A, or
      —NR$^b$R$^c$, wherein R$^b$ and R$^c$ are each independently
        hydrogen,
        hydroxy,
        C$_{1-6}$-alkyl,
          —S(O)$_2$—C$_{1-6}$-alkyl, or
          —C(O)—C$_{1-6}$-alkyl,
    —(CR$^{iii}$R$^{iv}$)$_n$—C(O)R$^d$,
      wherein R$^{iii}$ and R$^{iv}$ are independently from each other H, methyl, or ethyl;
      wherein n is from 0 to 4;
      wherein R$^d$ is
        C$_{1-6}$-alkoxy,
          —NR$^e$R$^f$, wherein R$^e$ and R$^f$ are each independently
            hydrogen,
            C$_{1-6}$-alkyl, or
            —(C$_{2-6}$-alkylene)-NR$^g$R$^h$; wherein R$^g$ and R$^h$ are each independently
              hydrogen, C$_{1-6}$-alkyl, or —C(O)O—C$_{1-6}$-alkyl, or
        phenyl, 5- to 6-membered heteroaryl, 3- to 7-membered heterocycloalkyl
        or 3 to 7-membered cycloalkyl,
          which are optionally substituted with one or more A,
    —S(O)$_2$-phenyl, wherein phenyl is optionally substituted with one or more halo, C$_{1-6}$-haloalkyl, C$_{1-6}$-alkyl, C$_{1-6}$-alkoxy, C$_{1-6}$-haloalkoxy, nitro, hydroxy or cyano;
    —S(O)$_2$—C$_{1-6}$-alkyl,
    —S(O)$_2$N(C$_{1-6}$-alkyl)$_2$, or
    —S(O)$_2$NH(C$_{1-6}$-alkyl);
A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$ C$_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)C$_{1-6}$-alkyl, —C(O)OR''', —C(O)R''', —C(O)NR'R'', —S(O)$_2$ NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$- cycloalkyl, or —(CH$_2$)$_x$—R''',
  wherein x is from 0 to 4,
  R' and R'' are each independently H or C$_{1-6}$-alkyl, or
  R' and R'' together with the nitrogen to which they are bound form a 5 or 6-membered heterocycle comprising one or two heteroatoms selected from N, O and S, and
  R''' is phenyl or 5- to 6-membered heteroaryl, optionally substituted with one, two, or three halo, C$_{1-6}$-haloalkyl, C$_{1-6}$-alkyl, or C$_{1-6}$-alkoxy,
R$^2$ is hydrogen,
  C$_{1-6}$-alkyl, or
  —C(O)R$^n$, wherein R$^n$ is
    C$_{1-6}$-alkyl,
    3 to 7-membered heterocycloalkyl, optionally substituted with one, two or three C$_{1-6}$-alkyl, —C(O)O—C$_{1-6}$-alkyl, or —S(O)$_2$—C$_{1-6}$-alkyl, or
    NR$^j$R$^k$, wherein R$^j$ and R$^k$ are each independently
      hydrogen,
      C$_{1-6}$-alkyl, or
      —(C$_{2-6}$-alkylene)-NR$^l$R$^m$; wherein R$^l$ and R$^m$ are each independently hydrogen, C$_{1-6}$-alkyl, or —C(O)O—C$_{1-6}$-alkyl;
R$^3$, R$^4$, R$^5$, R$^6$ are each independently hydrogen, halo, C$_{1-6}$-alkyl, halo-C$_{1-6}$-alkyl, C$_{1-6}$-alkoxy or C$_{1-6}$-haloalkoxy;

$R^7$, $R^8$, $R^9$, $R^{10}$ are each independently hydrogen, halo, $C_{1-6}$-alkyl, halo-$C_{1-6}$-alkyl, $C_{1-6}$-alkoxy or $C_{1-6}$-haloalkoxy;

or a pharmaceutically acceptable salt thereof, with the proviso that compounds wherein $R^1$, $R^2$, $R^3$, $R^4$, $R^5$ and $R^6$ are all simultaneously hydrogen are excluded.

The invention further encompasses an embodiment of formula (I) wherein

X is $CH_2$, and Y is C=O,
X is O, and Y is C=O, or
X—Y is N=N;

$R^1$ is H,
$C_{2-6}$-alkyl, optionally substituted with CN or OH,
$C_{1-6}$-haloalkyl,
—$(CR^iR^{ii})_m$—$R^a$,
wherein $R^i$ and $R^{ii}$ are independently from each other H, methyl, or ethyl;
wherein m is from 0 to 4;
wherein $R^a$ is
phenyl, 5- to 6-membered heteroaryl, 3- to 7-membered heterocycloalkyl
or 3 to 7-membered cycloalkyl,
which are optionally substituted with one or more A, or
—$NR^bR^c$, wherein $R^b$ and $R^c$ are each independently hydrogen, $C_{1-6}$-alkyl, —$S(O)_2$—$C_{1-6}$-alkyl, or —$C(O)$—$C_{1-6}$-alkyl,
—$(CR^{iii}R^{iv})_n$—$C(O)R^d$,
wherein $R^{iii}$ and $R^{iv}$ are independently from each other H, methyl, or ethyl;
wherein n is from 0 to 4;
wherein $R^d$ is
$C_{1-6}$-alkoxy,
—$NR^eR^f$, wherein $R^e$ and $R^f$ are each independently hydrogen,
$C_{1-6}$-alkyl, or
—$(C_{2-6}$-alkylene)$NR^gR^h$; wherein $R^g$ and $R^h$ are each independently
hydrogen, $C_{1-6}$-alkyl, or —$C(O)O$—$C_{1-6}$-alkyl,
or
phenyl, 5- to 6-membered heteroaryl, 3- to 7-membered heterocycloalkyl
or 3 to 7-membered cycloalkyl,
which are optionally substituted with one or more A,
—$S(O)_2$-phenyl, optionally substituted by halo,
—$S(O)_2$—$C_{1-6}$-alkyl,
—$S(O)_2N(C_{1-6}$-alkyl$)_2$, or
—$S(O)_2NH(C_{1-6}$-alkyl);

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, $C_{1-6}$-thioalkyl, —$S(O)_2$—$C_{1-6}$-alkyl, —$S(O)$—$C_{1-6}$-alkyl, nitro, hydroxy, cyano, —$(C_{1-6}$-alkylene)-O—$C_{1-6}$-alkyl, —$(C_{1-6}$-alkylene)-O—$C_{1-6}$-haloalkyl, —$C(O)O$—$C_{1-6}$-alkyl, —$C(O)NR'R''$, —$S(O)_2NR'R''$, —$(CH_2)_x$—$NR'R''$, —$(CH_2)_x$—$NR'C(O)$—$C_{1-6}$-alkyl, or —$(CH_2)_x$—$NR'S(O)_2$—$C_{1-6}$-alkyl,
wherein x is from 0 to 4 and
R' and R" are each independently H or $C_{1-6}$-alkyl, or
R' and R" together with the nitrogen to which they are bound form a 5 or 6-membered heterocycle comprising one or two heteroatoms selected from N, O and S,
—$(CH_2)_y$—$C_{3-6}$-cycloalkyl, —$(CH_2)_y$-benzyl, or —$(CH_2)_y$- phenyl,
wherein y is from 0 to 4, and
wherein benzyl or phenyl are optionally substituted with one, two, or
three halo, $C_{1-6}$-haloalkyl, $C_{1-6}$-alkyl, or $C_{1-6}$-alkoxy;

$R^2$ is hydrogen, or $C_{1-6}$-alkyl;
$R^3$, $R^4$, $R^5$, $R^6$ are each independently hydrogen, halo, $C_{1-6}$-alkyl, halo-$C_{1-6}$-alkyl, $C_{1-6}$-alkoxy or $C_{1-6}$-haloalkoxy;
$R^7$, $R^8$, $R^9$, $R^{10}$ are each independently hydrogen, halo, $C_{1-6}$-alkyl, halo-$C_{1-6}$-alkyl, $C_{1-6}$-alkoxy or $C_{1-6}$-haloalkoxy;

or a pharmaceutically acceptable salt thereof, with the proviso that compounds wherein $R^1$, $R^2$, $R^3$, $R^4$, $R^5$ and $R^6$ are all simultaneously hydrogen are excluded.

The invention further encompasses an embodiment of formula (I) wherein

X is $CH_2$, and Y is C=O,
X is O, and Y is C=O, or
X—Y is N=N;

$R^1$ is H,
$C_{2-6}$-alkyl, optionally substituted with CN or OH,
$C_{1-6}$-haloalkyl,
—$(CR^iR^{ii})_m$—$R^a$,
wherein $R^i$ and $R^{ii}$ are independently from each other H, methyl, or ethyl;
wherein m is from 1 to 4;
wherein $R^a$ is
phenyl, 5- to 6-membered heteroaryl, 3- to 7-membered heterocycloalkyl
or 3 to 7-membered cycloalkyl,
which are optionally substituted with one or more A, or
—$NR^bR^c$, wherein $R^b$ and $R^c$ are each independently hydrogen, $C_{1-6}$-alkyl, —$S(O)_2$—$C_{1-6}$-alkyl, or —$C(O)$—$C_{1-6}$-alkyl,
—$(CR^{iii}R^{iv})_n$—$C(O)R^d$,
wherein $R^{iii}$ and $R^{iv}$ are independently from each other H, methyl, or ethyl;
wherein n is from 0 to 4;
wherein $R^d$ is
$C_{1-6}$-alkoxy,
—$NR^eR^f$, wherein $R^e$ and $R^f$ are each independently hydrogen,
$C_{1-6}$-alkyl, or
—$(C_{2-6}$-alkylene)$NR^gR^h$; wherein $R^g$ and $R^h$ are each independently
hydrogen, $C_{1-6}$-alkyl, or —$C(O)O$—$C_{1-6}$-alkyl,
or
phenyl, 5- to 6-membered heteroaryl, 3- to 7-membered heterocycloalkyl
or 3 to 7-membered cycloalkyl,
which are optionally substituted with one or more A,
—$S(O)_2$—$C_{1-6}$-alkyl,
—$S(O)_2N(C_{1-6}$-alkyl$)_2$, or
—$S(O)_2NH(C_{1-6}$-alkyl);

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, $C_{1-6}$-thioalkyl, —$S(O)_2$—$C_{1-6}$-alkyl, cyano, —$CH_2OCH_3$, —$C(O)O$—$C_{1-6}$-alkyl, —$C(O)NR'R''$, —$S(O)_2NR'R''$, —$NR'C(O)$—$C_{1-6}$-alkyl, —$NR'S(O)_2$—$C_{1-6}$-alkyl, benzyl, or phenyl wherein R' and R" are each independently H or $C_{1-6}$-alkyl.
$R^2$ is hydrogen, or $C_{1-6}$-alkyl;
$R^3$, $R^4$, $R^5$, $R^6$ are each independently hydrogen, halo, $C_{1-6}$-alkyl, halo-$C_{1-6}$-alkyl, $C_{1-6}$-alkoxy or $C_{1-6}$-haloalkoxy;
$R^7$, $R^8$, $R^9$, $R^{10}$ are each independently hydrogen or halo;

or a pharmaceutically acceptable salt thereof, with the proviso that compounds wherein $R^1$, $R^2$, $R^3$, $R^4$, $R^5$ and $R^6$ are all simultaneously hydrogen are excluded.

Preferred compounds of formula (I-a) are

1-[1-(6-Chloro-1H-indole-3-carbonyl)-piperidin-4-yl]-1,3-dihydro-indol-2-one,

1-{1-[6-Chloro-1-(3,5-difluoro-benzyl)-1H-indole-3-carbonyl]-piperidin-4-yl}-1,3-dihydro-indol-2-one, 2-{6-Chloro-3-[4-(2-oxo-2,3-dihydro-indol-1-yl)-piperidine-1-carbonyl]-indol-1-yl}-N-methyl-acetamide, 2-(6-Chloro-3-{[4-(2-oxo-2,3-dihydro-1H-indol-1-yl)piperidin-1-yl]carbonyl}-1H-indol-1-yl)-N,N-dimethylacetamide, 2-{6-Chloro-3-[4-(2-oxo-2,3-dihydro-indol-1-yl)-piperidine-1-carbonyl]-indol-1-yl}-N,N-diethyl-acetamide, N-[2-(6-Chloro-3-{[4-(2-oxo-2,3-dihydro-1H-indol-1-yl)piperidin-1-yl]carbonyl}-1H-indol-1-yl)ethyl]methanesulfonamide, N-[2-(6-Chloro-3-{[4-(2-oxo-2,3-dihydro-1H-indol-1-yl)piperidin-1-yl]carbonyl}-1H-indol-1-yl)ethyl]acetamide, and 1-[1-(6-Chloro-2-methyl-1H-indole-3-carbonyl)-piperidin-4-yl]-1,3-dihydro-indol-2-one, 1-{1-[6-Chloro-1-(2-methylamino-ethyl)-1H-indole-3-carbonyl]-piperidin-4-yl}-1,3-dihydro-indol-2-one hydrochloride, or 1-{1-[6-Chloro-1-(2-dimethylamino-ethyl)-1H-indole-3-carbonyl]-piperidin-4-yl}-1,3-dihydro-indol-2-one.

Preferred compounds of formula (I-b) are

3-[1-(6-Chloro-1H-indole-3-carbonyl)-piperidin-4-yl]-3H-benzooxazol-2-one, and

2-{6-Chloro-3-[4-(2-oxo-benzooxazol-3-yl)-piperidine-1-carbonyl]-indol-1-yl}-N-methyl-acetamide.

Preferred compounds of formula (I-c) are

1-[1-(6-Chloro-1H-indole-3-carbonyl)-piperidin-4-yl]-1,3-dihydro-indol-2-one, 2-(3-{[4-(1H-Benzotriazol-1-yl)piperidin-1-yl]carbonyl}-6-chloro-1H-indol-1-yl)-N-methylacetamide, 2-(3-{[4-(1H-Benzotriazol-1-yl)piperidin-1-yl]carbonyl}-6-chloro-1H-indol-1-yl)-N,N-dimethylacetamide, (4-Benzotriazol-1-yl-piperidin-1-yl)-[6-chloro-1-(2-methylamino-ethyl)-1H-indol-3-yl]-methanone hydrochloride, (4-Benzotriazol-1-yl-piperidin-1-yl)-[6-chloro-1-(2-dimethylamino-ethyl)-1H-indol-3-yl]-methanone, and (4-Benzotriazol-1-yl-piperidin-1-yl)-(7-chloro-2-methyl-1,2,3,4-tetrahydro-pyrazino[1,2-a]indol-10-yl)-methanone.

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprises administering a therapeutically effective amount of a compound of formula (I), (Ia), (Ib), or (Ic).

The invention also encompasses a pharmaceutical composition comprising a compound of formula (I), (Ia), (Ib), or (Ic) and a pharmaceutically acceptable carrier. The pharmaceutical composition may further comprise at least one pharmaceutically acceptable excipient.

In a certain embodiment, the compounds of formula (I) of the invention can be manufactured according to a process comprising reacting a compound of formula (II):

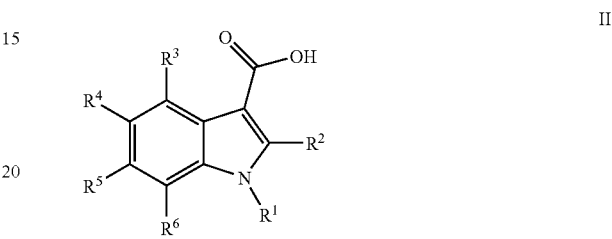

with a compound of formula (III):

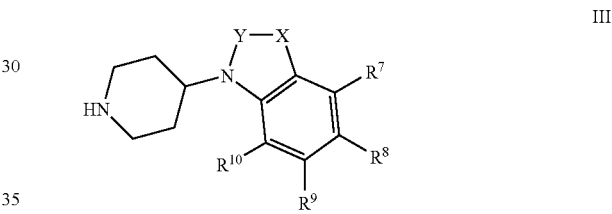

to obtain a compound of formula (I) wherein X, Y, $R^1$, $R^2$, $R^3$, $R^4$, $R^5$, $R^6$, $R^7$, $R^8$, $R^9$ and $R^{10}$ are as defined hereinabove for formula (I).

In another embodiment, the compounds of formula (I) of the invention can be manufactured according to a process comprising reacting a compound of formula (I-1), wherein $R^1$ equals H:

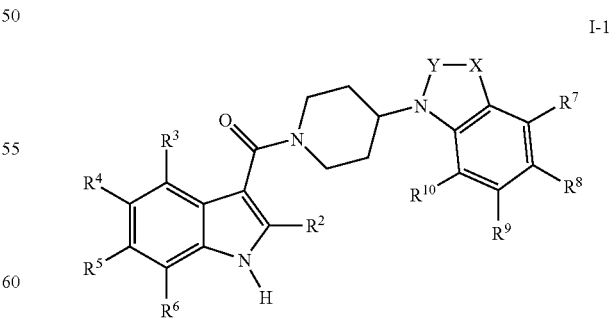

with a compound of formula $R^1$—Z (wherein $R^1$ is different from H), to obtain a compound of formula (I) wherein X, Y, $R^1$, $R^2$, $R^3$, $R^4$, $R^5$, $R^6$, $R^7$, $R^8$, $R^9$ and $R^{10}$ are as defined hereinabove for formula (I) and Z is halo.

These processes are described in more details with the following general schemes and procedures A to C.

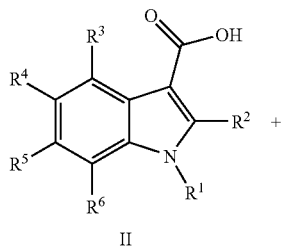

II

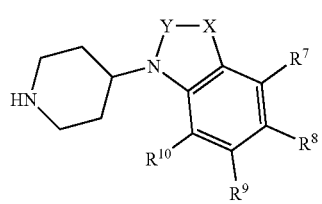

III

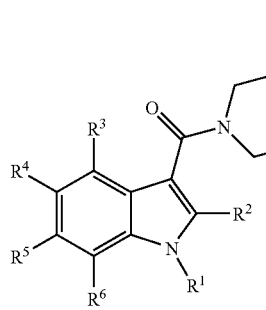

I

General Scheme A

Compounds of formula (I) can be prepared via an amide coupling between an indole 3-carboxylic acid (II) and a compound of formula (III). The usual reagents and protocols known in the art can be used to effect the amide coupling. Indole 3-carboxylic acids (II) are either commercially available or readily prepared using a procedure described in *J.* *Med. Chem.* 1991, 34, 140. Alternatively, they can be prepared following the general scheme C as described hereinafter. The compounds of formula (III) are either commercially available or prepared using methods known in the art starting from commercially available materials. General scheme A is hereinafter further illustrated with general procedures I and II.

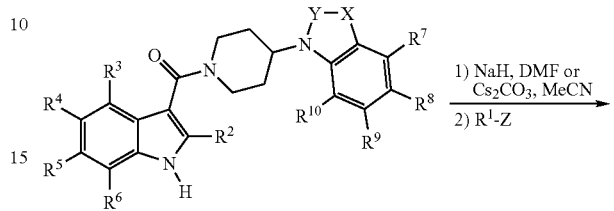

I-1

I

General Procedure B

Compounds of formula (I) with $R^1$ different from H can be prepared using methods known in the art, e.g. by N-deprotonation of a compound of formula (I-1) (compounds of formula (I) wherein $R^1$ is H) followed by treatment with an electrophilic reactant $R^1$—Z (wherein Z is a leaving group, e.g. halo) which is either commercially available or easily prepared according to methods well known in the art and commercially available starting materials. General scheme B is hereinafter further illustrated with general procedure III.

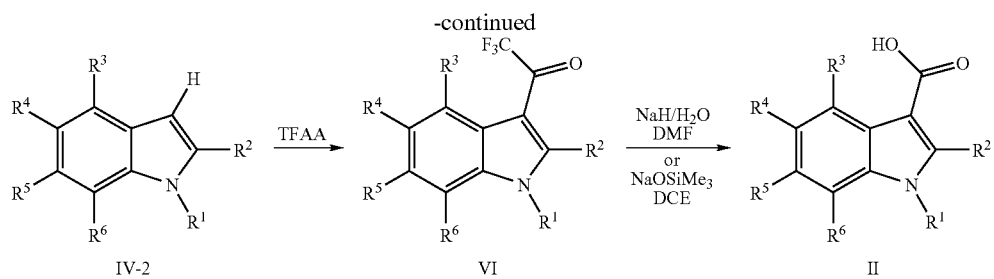

General Procedure C

The treatment of an indole derivative (IV-1) with trifluoroacetic anhydride in DMF affords intermediate (V) which can be hydrolysed with an aqueous sodium hydroxide solution to give the 3-carboxylic acid indole derivative (II-1). Alternatively, (V) could react with an electrophilic reactant $R^1$—Z to give (VI), which is then converted to the corresponding carboxylic acid derivative (II) with $NaH/H_2O$ in DMF (see *J. Org Chem.*, 1993, 10, 2862). Intermediate (VI) can alternatively be obtained by treatment of an indole derivative (IV-2) with trifluoroacetic anhydride in a suitable solvent, e.g. DMF, dichloromethane or 1,2-dichloroethane. Addition of a suitable base may be advantageous.

The compounds of the present invention exhibit V1a activity, which may be detected as described below:

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM $MgCl2$ adjusted to pH=7.4+ complete cocktail of protease inhibitor (Roche Diagnostics)); homogenized with Polytron for 1 min; and sonicated on ice for 2×2 minutes at 80% intensity (Vibracell sonicator). The preparation was centrifuged 20 min at 500 g at 4° C., the pellet was discarded and the supernatant centrifuged 1 hour at 43'000 g at 4° C. (19'000 rpm). The pellet was resuspended in 12.5 ml Lysis buffer+ 12.5 ml Sucrose 20% and homogenized using a Polytron for 1-2 min. The protein concentration was determined by the Bradford method and aliquots were stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM $CaCl2$, 10 mM $MgCl2$) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin and for compound testing 100 ul of a serial dilution of each compound in 2% DMSO. The plate was incubated 1 h at room temperature, centrifuged 1 min at 1000 g and counted on a Packard Top-Count. Non-specific binding counts were subtracted from each well, and data was normalized to the maximum specific binding set at 100%. To calculate an IC 50 the curve was fitted using a non-linear regression model (XLfit), and the Ki was calculated using the Cheng-Prussoff equation.

| Example No | pKi hV1a |
|---|---|
| 1 | 8.05 |
| 2 | 8.59 |
| 3 | 8.74 |
| 4 | 8.89 |
| 5 | 7.93 |
| 6 | 8.5 |
| 7 | 7.93 |
| 8 | 7.9 |
| 10 | 8.17 |
| 13 | 7.85 |
| 14 | 8.18 |
| 15 | 8.68 |
| 17 | 7.71 |
| 18 | 7.68 |

The present invention also provides pharmaceutical compositions containing compounds of the invention, for example compounds of formulae (I-a) to (I-e), or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

Example A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition can be manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

Example C

Suppositories of the following composition can be manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C.

Thereupon, the finely powdered active substance can be added thereto and stirred until it has dispersed completely. The mixture can be poured into suppository moulds of suitable size, left to cool; the suppositories then can be removed from the moulds and packed individually in wax paper or metal foil.

In the following, the synthesis of compounds of formula (I) is further exemplified: The compounds of formula I may be prepared in accordance with the process variants as described above. The starting materials described in the Example section are either commercially available or are otherwise known or derived from the chemical literature, for instance as cited below, or may be prepared as described in the Examples section.

Examples

Acid Intermediates of Formula II and II-1

Acid 1

6-Chloro-1H-indole-3-carboxylic acid a) 1-(6-Chloro-1H-indol-3-yl)-2,2,2-trifluoro-ethanone To a solution of 1.0 g (6.6 mmol) 6-chloroindole in 13 ml DMF were added dropwise at 0° C. 2.75 ml (19.8 mmol) trifluoroacetic anhydride. Stirring at this temperature for 90 min. was followed by quenching with 30 ml of a 2 M aqueous solution of sodium carbonate, dilution with 50 ml water and extraction with three 100-ml portions of tert-butyl methyl ether. The combined organic layers were dried over sodium sulfate, filtered and concentrated to give 1.3 g (80%) of the crude title compound as an off-white solid.

ES-MS m/e (%): 246 (M−H+).

b) 6-Chloro-1H-indole-3-carboxylic acid

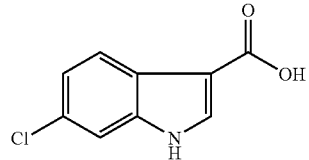

A mixture of 1.3 g (5.3 mmol) 1-(6-chloro-1H-indol-3-yl)-2,2,2-trifluoro-ethanone and 26.5 ml of a 4 M aqueous solution of sodium hydroxide was heated at reflux for 4.5 h. The mixture was cooled to room temperature and washed with two 100-ml portions of tert-butyl methyl ether. The aqueous layer was acidified to pH 2-3 by addition of concentrated hydrochloric acid solution at 0° C. Extraction with three 100-ml portions of tert-butyl methyl ether, drying over sodium sulfate, filtration and concentration in vacuo gave 0.80 g (78%) of the crude title compound as a brown solid.

ES-MS m/e (%): 194 (M−H+).

Acid 2

6-Chloro-1-(3,5-difluoro-benzyl)-1H-indole-3-carboxylic acid a) 1-[6-Chloro-1-(3,5-difluoro-benzyl)-1H-indol-3-yl]-2,2,2-trifluoro-ethanone A mixture of 2.0 g (9.4 mmol) 1-(6-chloro-1H-indol-3-yl)-2,2,2-trifluoro-ethanone, 4.59 g (14.1 mmol) cesium carbonate and 2.14 g (10.4 mmol) 3,5-difluorobenzyl bromide in 90 ml acetonitrile was heated at 80° C. for 3 h. After cooling to room temperature addition of 150 ml water was followed by extraction with three 150-ml portions of tert-butyl methyl ether. The combined organic layers were dried over sodium sulfate, filtered and concentrated in vacuo. The residue was triturated in 30 ml hot cyclohexane. Filtration gave 2.2 g (64%) of the crude title compound as light brown solid.
ES-MS m/e (%): 372 (M−H$^+$).

b) 6-Chloro-1-(3,5-difluoro-benzyl)-1H-indole-3-carboxylic acid

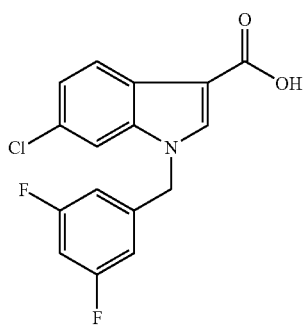

To a solution of 2.2 g (6.5 mmol) 1-[6-chloro-1-(3,5-difluoro-benzyl)-1H-indol-3-yl]-2,2,2-trifluoro-ethanone in 65 ml DMF were added 1.7 g (36 mmol) sodium hydride (50% in oil) at room temperature. After stirring for 5 min. 0.59 ml (33 mmol) water were added dropwise. Stirring was continued at room temperature for 45 min. The reaction mixture was diluted with 150 ml of tert-butyl methyl ether and extracted with two 150-ml portions of a 1 M aqueous solution of sodium hydroxide. The combined aqueous layers were acidified to pH 1 with concentrated hydrochloric acid solution and extracted with three 150-ml portions of ethyl acetate. The combined organic extracts were dried over sodium sulfate, filtered and concentrated in vacuo. The residue was dried in high vacuo at 80° C. to give 2.0 g (95%) of the crude title compound as a brown solid.
ES-MS m/e (%): 320 (M−H$^+$).

Acid 3

6-Chloro-1-methylcarbamoylmethyl-1H-indole-3-carboxylic acid

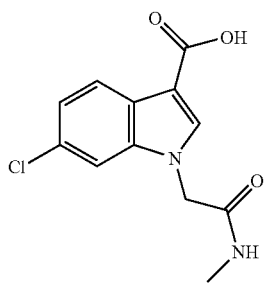

a) 2-[6-Chloro-3-(2,2,2-trifluoro-acetyl)-indol-1-yl]-N-methyl-acetamide

Following general procedure II, the alkylation of 1-(6-chloro-1H-indol-3-yl)-2,2,2-trifluoro-ethanone, with (commercially available) 2-chloro-N-methyl-acetamide gave the title compound.
ES-MS m/e (%): 319.3 (M+H$^+$).

b) 6-Chloro-1-methylcarbamoylmethyl-1H-indole-3-carboxylic acid

2-[6-Chloro-3-(2,2,2-trifluoro-acetyl)-indol-1-yl]-N-methyl-acetamide was suspensed in DCE and treated with (2.2 eq.) of sodium trimethylsilanolate. After shaking at room temperature for 20 min, the mixture was concentrated in vacuo and purified by prep. HPLC to give the title compound in 27% yield.
ES-MS m/e (%): 265.0 (M−H$^+$).

Acid 4

6-Chloro-1-dimethylcarbamoylmethyl-1H-indole-3-carboxylic acid

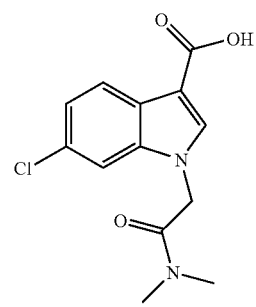

a) 2-[6-Chloro-3-(2,2,2-trifluoro-acetyl)-indol-1-yl]-N,N-dimethyl-acetamide

To a stirred solution of 1-(6-chloro-1H-indol-3-yl)-2,2,2-trifluoro-ethanone (0.75 g) in 20 ml of DMF at 0° C., were added 128 mg (1.1 eq.) of NaH (60% in oil). The mixture was stirred for 30 min. and then 0.32 ml (1.1 eq.) of dimethylamino-acetyl chloride were added. The mixture was stirred an additional hour and then poured onto water and extracted with ethyl acetate. The combined organic phases were dried over Na$_2$SO$_4$ and concentrated in vacuo to afford 598 mg (61%) of 2-[6-chloro-3-(2,2,2-trifluoro-acetyl)-indol-1-yl]-N,N-dimethyl-acetamide as a white solid.

b) 6-Chloro-1-dimethylcarbamoylmethyl-1H-indole-3-carboxylic acid

Using the procedure described for the preparation of 6-chloro-1-(3,5-difluoro-benzyl)-1H-indole-3-carboxylic acid, from 0.50 g of 2-[6-chloro-5-methyl-3-(2,2,2-trifluoro-acetyl)-indol-1-yl]-N,N-dimethyl-acetamide were prepared 0.38 g (76%) of 6-chloro-1-dimethylcarbamoylmethyl-1H-indole-3-carboxylic acid as a white solid.

Acid 5

6-Chloro-2-methyl-1H-indole-3-carboxylic acid a) (6-Chloro-1H-indol-2-yl)-methanol To a solution of 2.00 g (8.94 mmol) 6-chlorindole-2-carboxylic acid ethyl ester in 50 ml diethyl ether were added 0.475 g (12.5 mmol) lithium aluminum hydride at 0° C. The reaction mixture was heated at reflux for 45 min and quenched by consecutive addition of 10 ml water, 10 ml aqueous 2 M sodium hydroxide solution and 10 ml water at 0° C. The aqueous layer was extracted with tert-butyl methyl ether (3×100 ml). The combined organic layers were dried over sodium sulfate and concentrated in vacuo to give the crude title compound (1.64 g; 100%) as a white solid.

MS m/e (%): 180 (M–H$^+$, 100).

b) 6-Chloro-2-methyl-1H-indole

A solution of 1.60 g (8.81 mmol) (6-chloro-1H-indol-2-yl)-methanol in 5 ml 1,2-dichloroethane was added to a mixture of 80.0 ml trifluoroacetic acid and 32.0 ml triethylsilane at 65° C. After 5 min, the reaction mixture was cooled to room temperature and quenched with water. The pH was adjusted to 14 by the addition of aqueous sodium hydroxide solution (32%). The aqueous layer was extracted with tert-butyl methyl ether (3×200 ml). The combined organic layers were dried over sodium sulfate and concentrated in vacuo. The residue was purified by flash-chromatography (aminopropyl-modified silica gel, n-heptane/ethyl acetate) to give the title compound (0.39 g; 27%) as a white solid.

MS m/e (%): 164 (M–H$^+$, 100).

c) 1-(6-Chloro-2-methyl-1H-indol-3-yl)-2,2,2-trifluoro-ethanone

To a solution of 0.38 g (2.3 mmol) 6-chloro-2-methyl-1H-indole in 20 ml 1,2-dichloroethane at 0° C. were added 0.35 ml (2.5 mmol) trifluoroacetic anhydride. The reaction mixture was quenched with aqueous 2 M sodium carbonate solution after 30 min and extracted with dichloromethane (3×100 ml). The combined organic layers were dried over sodium sulfate and concentrated in vacuo to give the title compound (0.57 g; 95%) as an off-white solid.

MS m/e (%): 260 (M–H$^+$, 100).

d) 6-Chloro-2-methyl-1H-indole-3-carboxylic acid

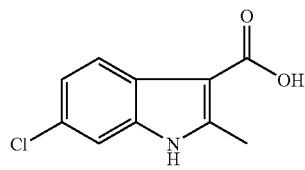

A solution of 0.57 g (2.2 mmol) 1-(6-chloro-2-methyl-1H-indol-3-yl)-2,2,2-trifluoro-ethanone in 21.7 ml (86.8 mmol) aqueous 4 M sodium hydroxide solution was heated at reflux for 45 min. After cooling to room temperature the reaction mixture was diluted with water and extracted with tert-butyl methyl ether (2×50 ml). The aqueous layer was cooled to 0-5° C., acidified (pH 1-2) with concentrated aqueous hydrochloric acid solution and extracted with ethyl acetate (3×100 ml). The combined ethyl acetate layers were dried over sodium sulfate and concentrated in vacuo to give the title compound (0.14 g, 31%) as an off-white solid.

MS m/e (%): 208 (M–H$^+$, 100).

Acid 6

1-[2-(tert-Butoxycarbonyl-methyl-amino)-ethyl]-6-chloro-1H-indole-3-carboxylic acid a) {2-[6-Chloro-3-(2,2,2-trifluoro-acetyl)-indol-1-yl]-ethyl}-carbamic acid tert-butyl ester To a solution of 11.5 g (46.4 mmol) 1-(6-chloro-1H-indol-3-yl)-2,2,2-trifluoro-ethanone in 150 ml N,N-dimethylformamide were slowly added 6.25 g (55.7 mmol) potassium tert-butylate. The temperature was kept below 32° C. The reaction mixture was allowed to cool to room temperature and stirred for 20 min. To the resulting brown suspension were added slowly 12.4 g (55.7 mmol) 2,2-dioxo-2$\lambda^6$-[1,2,3]oxathiazolidine-3-carboxylic acid tert-butyl ester. The reaction mixture was stirred at room temperature until complete consumption of 1-(6-chloro-1H-indol-3-yl)-2,2,2-trifluoro-ethanone, which was monitored by thin layer chromatography. Dilution with 300 ml tert-butyl methyl ether was followed by washing with 250 ml of a 0.2 M aqueous solution of hydrochloric acid. The aqueous layer was extracted with two 200-ml portions of tert-butyl methyl ether. The combined organic layers were washed with water and brine, dried over sodium sulfate and concentrated in vacuo. The residue, 19.5 g of a light brown solid, was triturated with 300 ml of warm tert-butyl methyl ether. After cooling to room temperature the precipitate was collected by filtration, washed with cold tert-butyl methyl ether and dried in vacuo to give 11.1 g (61%) of the title compound as an off-white solid. The filtrate was concentrated to dryness. The residue was triturated with 50 ml warm tert-butyl methyl ether. After cooling to room temperature the precipitate was collected by filtration, washed with cold tert-butyl methyl ether and dried in vacuo to give another 3.5 g (19%) of the title compound as an off-white solid.

MS m/e (%): 387 (M–H$^+$, 87).

b) {2-[6-Chloro-3-(2,2,2-trifluoro-acetyl)-indol-1-yl]-ethyl}-methyl-carbamic acid tert-butyl ester To a solution of 14.1 g (36.1 mmol) {2-[6-chloro-3-(2,2,2-trifluoro-acetyl)-indol-1-yl]-ethyl}-carbamic acid tert-butyl ester in 360 ml dry tetrahydrofuran were slowly added 44 ml (40 mmol) of a 0.91 M solution of potassium hexamethyldisilazide in tetrahydrofuran at –78° C. After stirring for 20 min. were added 2.5 ml (40 mmol) iodomethane at –78° C. Stirring was continued for 15 min. at –78° C. The cooling bath was removed and the mixture was stirred for another 3 h at room temperature. Quenching with water was followed by evaporation of the solvent in a rotary evaporator. The residue was diluted with a mixture of 200 ml water and 100 ml of a saturated aqueous solution of ammonium chloride. After extraction with three 250-ml portions of tert-butyl methyl ether the combined organic extracts were washed with 200 ml of an ice-cold 0.2 M aqueous solution of hydrochloric acid and 100 ml brine, dried over sodium sulfate and concentrated in vacuo to give 14.9 g of the crude product as a brown oil.

MS m/e (%): 349 ((M-C4H8)+H$^+$, 100).

c) 1-[2-(tert-Butoxycarbonyl-methyl-amino)-ethyl]-6-chloro-1H-indole-3-carboxylic acid

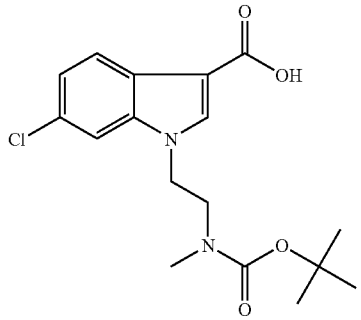

To a solution of 15.4 g (38.0 mmol) crude {2-[6-chloro-3-(2,2,2-trifluoro-acetyl)-indol-1-yl]-ethyl}-methyl-carbamic acid tert-butyl ester in 380 ml N,N-dimethylformamide were slowly added 11.0 g (228 mmol) sodium hydride (50%, dispersion in oil) followed by 3.40 ml (190 mmol) water at 15-22° C. After stirring for 1 h at room temperature 500 ml water were added slowly. The mixture was washed with two 300-ml portions of tert-butyl methyl ether. The combined organic layers were extracted with 300 ml of a 0.5 M aqueous solution of sodium hydroxide. The combined aqueous layers were acidified to pH 2 with an ice-cold 4 M aqueous solution of hydrochloric acid at 0-5° C. and extracted with two 400-ml portions of ethyl acetate.

The organic extracts were dried over sodium sulfate and concentrated in vacuo to give 11.3 g (84.3%) of the title compound as a light yellow solid.

MS m/e (%): 351 (M−H+, 100).

Examples

Amide Coupling:
General procedure I:
To a stirred solution of an indole-3-carboxylic acid derivative (1 mmol) in 10 ml CH$_2$Cl$_2$ are added (1.3 mmol) EDC, (1.3 mmol) HOBt, (1.3 mmol) triethylamine and (1 mmol) of the amine derivative. The mixture is stirred overnight at RT and then poured onto water and extracted with CH$_2$Cl$_2$. The combined organic phases are dried over Na$_2$SO$_4$ and concentrated in vacuo. Flash chromatography or preparative HPLC affords an amide derivative of formula (I).

General Procedure II:
To a solution of an indole-3-carboxylic acid derivative (0.13 mmol), N-ethyl diisopropyl amine (0.14 mmol) and TBTU or HATU (0.14 mmol) in 2 ml dry N,N-dimethylformamide is added the amine derivative (0.14 mmol) at RT. The reaction mixture is quenched with 0.5 M aqueous sodium hydroxide (20 ml) after 2 h and extracted with ethyl acetate (2×30 ml). The combined organic layers are washed with water (2×30 ml) and brine (1×30 ml), dried over sodium sulfate and concentrated to dryness. Flash chromatography or preparative HPLC affords an amide derivative of formula (I).

Indole-N-alkylation:
General Procedure III:
To a stirred solution of an indole of formula (I-1) wherein R$^1$ is H in DMF are added 2. 1 eq. NaH (60% in oil). The mixture is stirred at RT for 30 min. and then the electrophilic reagent R$^1$—Z (1.1 eq.) is added. The mixture is stirred an additional 14 hours at 60° C. and then poured onto water and extracted with ethyl acetate. The combined organic phases are dried over Na$_2$SO$_4$ and concentrated in vacuo. Purification by preparative HPLC affords compounds of formula (I) with R$^1$ different from H.

Example 1

1-[1-(6-Chloro-1H-indole-3-carbonyl)-piperidin-4-yl]-1,3-dihydro-indol-2-one

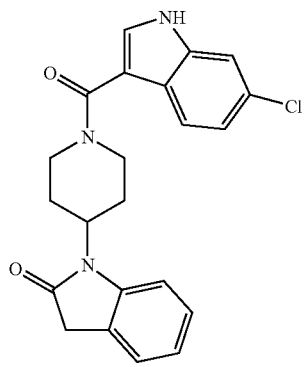

Amide coupling according to general procedure I:
Amine: 1-Piperidin-4-yl-1,3-dihydro-indol-2-one,
Acid: 6-Chloro-1H-indole-3-carboxylic acid,
ES-MS m/e (%): 393.9 (M+H+).

Example 2

1-{1-[6-Chloro-1-(3,5-difluoro-benzyl)-1H-indole-3-carbonyl]-piperidin-4-yl}-1,3-dihydro-indol-2-one

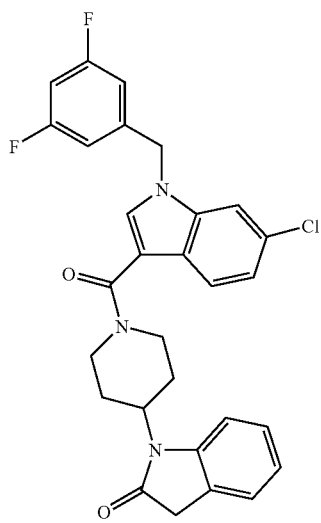

To a suspension of 0.10 g (0.31 mmol) 6-chloro-1-(3,5-difluoro-benzyl)-1H-indole-3-carboxylic acid and one drop of DMF in 2 ml dichloromethane were added dropwise at 0° C. 0.032 ml (0.37 mmol) oxalyl chloride. The mixture was allowed to warm to room temperature, stirred for 1 h and subsequently added dropwise to a solution of 74 mg (0.34 mmol) 1-piperidin-4-yl-1,3-dihydro-indol-2-one and 63 mg (0.62 mmol) triethylamine in 1 ml dichloromethane at room temperature. After stirring over night the reaction mixture was concentrated and the residue was purified by flash chromatography to give 78 mg (48%) of the title compound as a light yellow solid.

ES-MS m/e (%): 521 (M+H$^+$).

Example 3

2-{6-Chloro-3-[4-(2-oxo-2,3-dihydro-indol-1-yl)-piperidine-1-carbonyl]-indol-1-yl}-N-methyl-acetamide

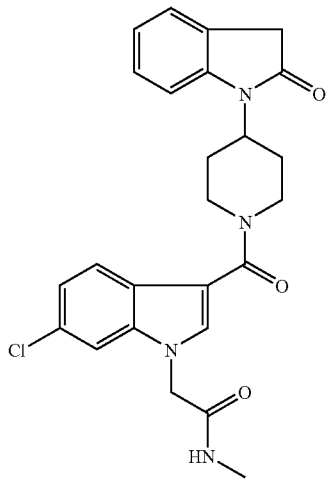

Amide coupling according to general procedure II:
Amine: 1-Piperidin-4-yl-1,3-dihydro-2H-indol-2-one,
Acid: 6-Chloro-1-methylcarbamoylmethyl-1H-indole-3-carboxylic acid,
ES-MS m/e (%): 465 (M+H$^+$, 100).

Example 4

2-(6-Chloro-3-{[4-(2-oxo-2,3-dihydro-1H-indol-1-yl)piperidin-1-yl]carbonyl}-1H-indol-1-yl)-N,N-dimethylacetamide

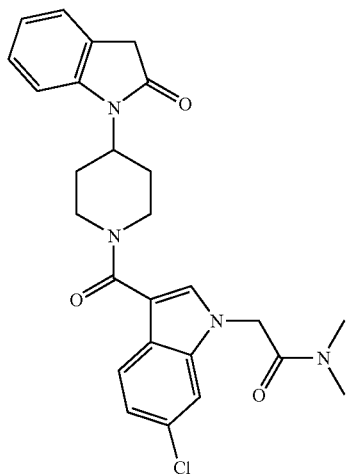

Amide coupling according to general procedure I:
Amine: 1-Piperidin-4-yl-1,3-dihydro-indol-2-one (CAS: 16223-25-9),
Acid: 6-Chloro-1-dimethylcarbamoylmethyl-1H-indole-3-carboxylic acid,
ES-MS m/e (%): 479.2 (M+H$^+$).

Example 5

2-{6-Chloro-3-[4-(2-oxo-2,3-dihydro-indol-1-yl)-piperidine-1-carbonyl]-indol-1-yl}-N,N-diethyl-acetamide

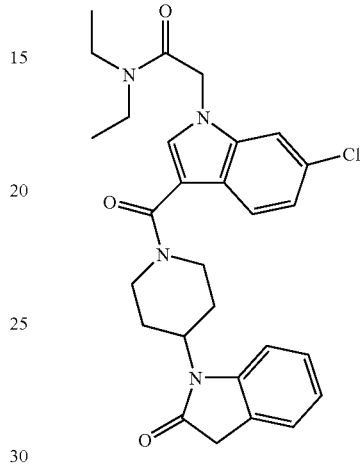

A solution of 1-[1-(6-chloro-1H-indole-3-carbonyl)-piperidin-4-yl]-1,3-dihydroindol-2-one (1 eq) in dry DMF was treated with NaH (1.1 eq) at RT for 15 mins and then a solution of 2-chloro-N,N-diethyl-acetamide (3.3 eq) and triethylamine (3.3 eq) in three portions and the mixture heated to 60° C. for 6 h. Concentration and purification by prep HPLC gave the title compound.

ES-MS m/e (%): 507.5 (M+H$^+$).

Example 6

N-[2-(6-Chloro-3-{[4-(2-oxo-2,3-dihydro-1H-indol-1-yl)piperidin-1-yl]carbonyl}-1H-indol-1-yl) ethyl]methanesulfonamide

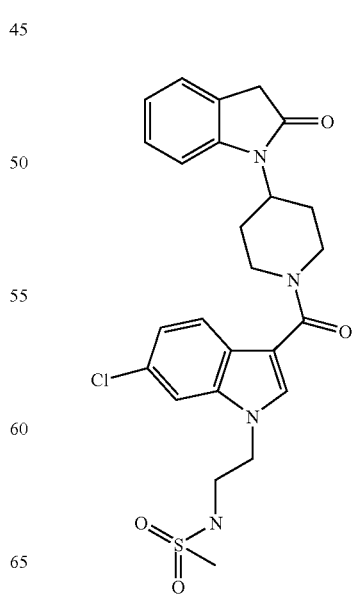

a) 1-{1-[1-(2-Amino-ethyl)-6-chloro-1H-indole-3-carbonyl]-piperidin-4-yl}-1,3-dihydro-indol-2-one A solution of 1-[1-(6-chloro-1H-indole-3-carbonyl)-piperidin-4-yl]-1,3-dihydro-indol-2-one (1 eq) in dry DMF was treated with NaH (1.1 eq) at 0° C. for 60 min. and then a solution of 2,2-dioxo-2λ6-[1,2,3]oxathiazolidine-3-carboxylic acid tert-butyl ester (1.1 eq) and triethylamine (1.1 eq) in dry DMF was added and the mixture stirred at RT for 2 h. After concentration the mixture was treated with 4 M HCl in dioxan (5 eq) at 50° C. for 1 h, evaporated to dryness and partitioned between ethyl acetate and 1 N NaHCO$_3$. The organic layer was washed with brine, separated, evaporated and the crude product chromatographed on silica gel (CH$_2$Cl$_2$-MeOH) to give the title compound.

ES-MS m/e (%): 437.0 (M+H$^+$).

b) N-[2-(6-Chloro-3-{[4-(2-oxo-2,3-dihydro-1H-indol-1-yl)piperidin-1-yl]carbonyl}-1H-indol-1-yl)ethyl]methanesulfonamide A solution of 1-{1-[1-(2-amino-ethyl)-6-chloro-1H-indole-3-carbonyl]-piperidin-4-yl}-1,3-dihydro-indol-2-one (1 eq) in dry CH$_2$Cl$_2$ was treated with methanesulfonyl chloride (1.1 eq) and triethylamine at RT for 15 h. Quenching with H$_2$O and extraction into CH$_2$Cl$_2$ followed by concentration and purification by prep HPLC gave the title compound.

ES-MS m/e (%): 515.2 (M+H$^+$).

Example 7

N-[2-(6-Chloro-3-{[4-(2-oxo-2,3-dihydro-1H-indol-1-yl)piperidin-1-yl]carbonyl}-1H-indol-1-yl)ethyl]acetamide

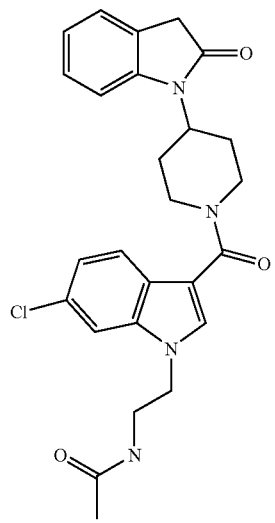

A solution of 1-{1-[1-(2-amino-ethyl)-6-chloro-1H-indole-3-carbonyl]-piperidin-4-yl}-1,3-dihydro-indol-2-one (1 eq) in dry CH$_2$Cl$_2$ was treated with acetyl chloride (1.1 eq) and triethylamine at RT for 15 h. Quenching with H$_2$O and extraction into CH$_2$Cl$_2$ followed by concentration and purification by prep HPLC gave the title compound.

ES-MS m/e (%): 479.2 (M+H$^+$).

Example 8

1-[1-(6-Chloro-2-methyl-1H-indole-3-carbonyl)-piperidin-4-yl]-1,3-dihydro-indol-2-one

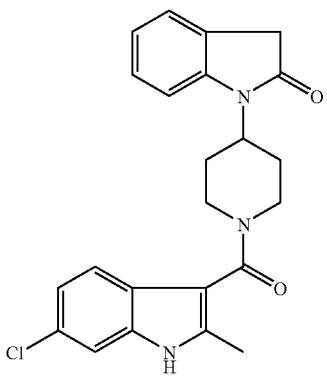

Amide coupling according to general procedure II:
Amine: 1-Piperidin-4-yl-1,3-dihydro-2H-indol-2-one,
Acid: 6-Chloro-2-methyl-1H-indole-3-carboxylic acid,
ES-MS m/e (%): 406 (M−H$^+$, 100).

Example 9

3-[1-(6-Chloro-1H-indole-3-carbonyl)-piperidin-4-yl]-3H-benzooxazol-2-one

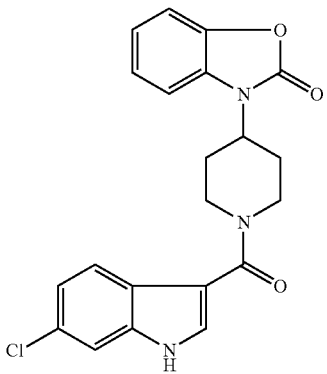

Amide coupling according to general procedure II:
Amine: 3-Piperidin-4-yl-3H-benzooxazol-2-one (preparation described in WO 95/28397),
Acid: 6-Chloro-1H-indole-3-carboxylic acid,
ES-MS m/e (%): 394 (M−H$^+$, 100).

Example 10

2-{6-Chloro-3-[4-(2-oxo-benzooxazol-3-yl)-piperidine-1-carbonyl]-indol-1-yl}-N-methyl-acetamide

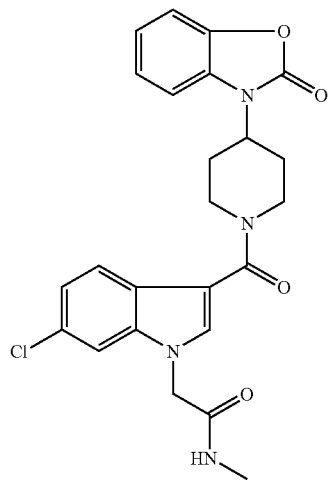

Amide coupling according to general procedure II:

Amine: 3-Piperidin-4-yl-3H-benzooxazol-2-one (preparation described in WO 95/28397), Acid: 6-Chloro-1-methylcarbamoylmethyl-1H-indole-3-carboxylic acid, ES-MS m/e (%): 467 (M+H$^+$, 100).

Example 11

1-[1-(6-Chloro-1H-indole-3-carbonyl)-piperidin-4-yl]-1,3-dihydro-indol-2-one

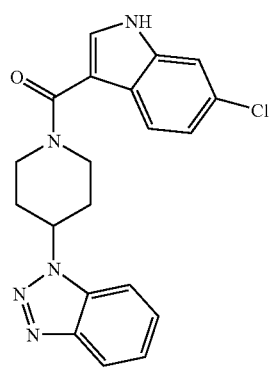

Amide coupling according to general procedure I:

Amine: (4-Benzotriazol-1-yl-piperidin-1-yl)-(6-chloro-1H-indol-3-yl)-methanone,

Acid: 6-Chloro-1H-indole-3-carboxylic acid,

ES-MS m/e (%): 380.4 (M+H$^+$).

Example 12

2-(3-{[4-(1H-Benzotriazol-1-yl)piperidin-1-yl]carbonyl}-6-chloro-1H-indol-1-yl)-N-methylacetamide

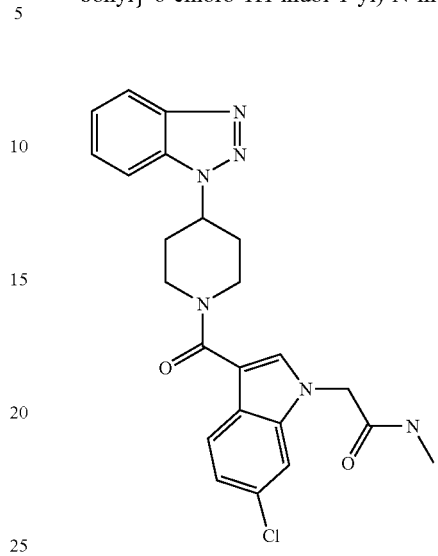

Amide coupling according to general procedure I:

Amine: 1-[1-(6-Chloro-1H-indole-3-carbonyl)-piperidin-4-yl]-1,3-dihydro-indol-2-one, Acid: 6-Chloro-1-methylcarbamoylmethyl-1H-indole-3-carboxylic acid acid, ES-MS m/e (%): 451.2 (M+H$^+$).

Example 13

2-(3-{[4-(1H-Benzotriazol-1-yl)piperidin-1-yl]carbonyl}-6-chloro-1H-indol-1-yl)-N,N-dimethylacetamide

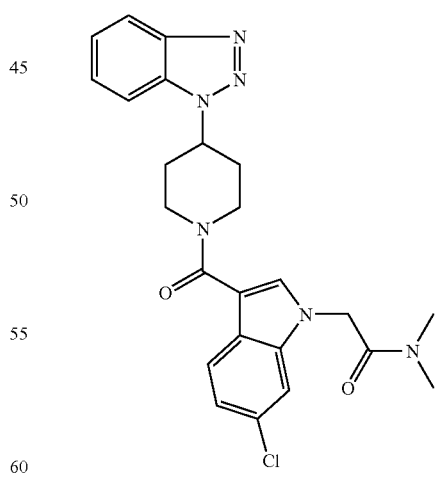

Amide coupling according to general procedure I:

Amine: 1-Piperidin-4-yl-1H-benzotriazole,

Acid: 6-Chloro-1-dimethylcarbamoylmethyl-1H-indole-3-carboxylic acid,

ES-MS m/e (%): 465.1 (M+H$^+$).

Example 14

1-{1-[6-Chloro-1-(2-methylamino-ethyl)-1H-indole-3-carbonyl]-piperidin-4-yl}-1,3-dihydro-indol-2-one hydrochloride a) (2-{6-Chloro-3-[4-(2-oxo-2,3-dihydro-indol-1-yl)-piperidine-1-carbonyl]-indol-1-yl}-ethyl)-methyl-carbamic acid tert-butyl ester To a solution of 0.20 g (0.57 mmol) 1-[2-(tert-butoxycarbonyl-methyl-amino)-ethyl]-6-chloro-1H-indole-3-carboxylic acid, 0.11 ml (0.63 mmol) N,N-diisopropylethylamine and 2 drops of N,N-dimethylformamide in 4 ml dicholormethane were added 0.060 ml (0.74 mmol) oxalyl chloride at 0-5° C. After completed addition the reaction mixture was allowed to warm to room temperature and stirred for 3 h. A solution of 0.15 g (0.68 mmol) 1,3-dihydro-1-(piperidin-4-yl)-(2H)-indol-2-one and 0.11 ml (0.63 mmol) N,N-diisopropylethylamine in 2 ml dicholormethane was added. After stirring for 15 min at room temperature silica gel was added to the reaction mixture and the solvent was evaporated in vacuo. The residue was transferred to a silica gel column. Elution gave 0.26 g (82%) of the title compound as an off-white solid.

ES-MS m/e (%): 551 (M+H$^+$, 39).

b) 1-{1-[6-Chloro-1-(2-methylamino-ethyl)-1H-indole-3-carbonyl]-piperidin-4-yl}-1,3-dihydro-indol-2-one hydrochloride

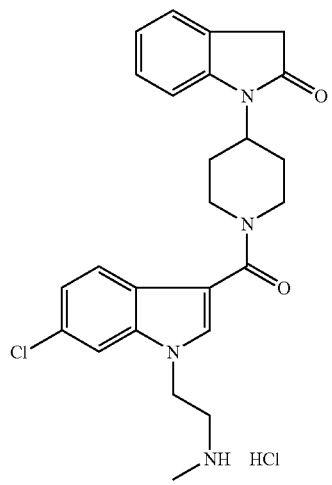

A solution of 0.25 g (0.45 mmol) (2-{6-chloro-3-[4-(2-oxo-2,3-dihydro-indol-1-yl)-piperidine-1-carbonyl]-indol-1-yl}-ethyl)-methyl-carbamic acid tert-butyl ester in 3.6 ml (4.5 mmol) of a 1.25 M solution of hydrochloric acid in methanol was stirred for 20 min. at 50° C. The reaction mixture was concentrated to dryness to give 0.21 g of the title compound as an off-white solid.

ES-MS m/e (%): 451 (M+H$^+$, 100).

Example 15

1-{1-[6-Chloro-1-(2-dimethylamino-ethyl)-1H-indole-3-carbonyl]-piperidin-4-yl}-1,3-dihydro-indol-2-one

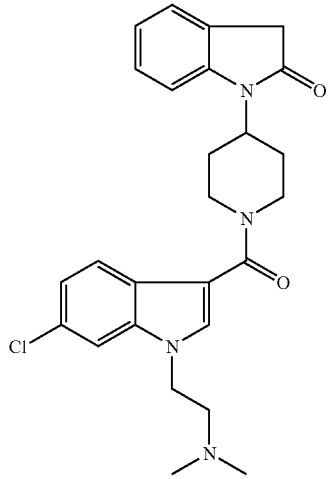

A suspension of 0.40 g (1.0 mmol) 1-[1-(6-chloro-1H-indole-3-carbonyl)-piperidin-4-yl]-1,3-dihydro-indol-2-one, 0.16 g (1.1 mmol) 1-chloro-2-dimethylaminoethane hydrochloride and 0.69 g (2.1 mmol) cesium carbonate in 10 ml acetonitrile was heated at 50° C. over night. After cooling to room temperature the reaction mixture was diluted with a 0.5 M aqueous solution of sodium hydroxide and extracted with three portions of ethyl acetate. The combined organic extracts were washed with brine, dried over sodium sulfate and concentrated in vacuo. Flash chromatography gave 0.18 g (39%) of the title compound.

ES-MS m/e (%): 466 (M+H$^+$, 100).

Example 16

(4-Benzotriazol-1-yl-piperidin-1-yl)-[6-chloro-1-(2-methylamino-ethyl)-1H-indol-3-yl]-methanone hydrochloride

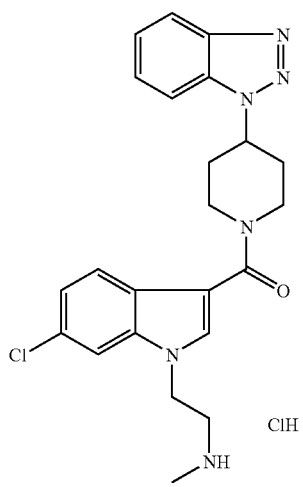

The title compound was prepared according to the procedures described for the preparation of 1-{1-[6-chloro-1-(2-methylamino-ethyl)-1H-indole-3-carbonyl]-piperidin-4-yl}-1,3-dihydro-indol-2-one using 1-(4-piperidyl)-1H-1,2,3-benzotriazole hydrochloride instead of 1,3-dihydro-1-(piperidin-4-yl)-(2H)-indol-2-one and a total of 3.2 molar equivalents of N,N-diisopropylethylamine instead of 2.2 molar equivalents in step a).

ES-MS m/e (%): 437 (M+H⁺, 100).

Example 17

(4-Benzotriazol-1-yl-piperidin-1-yl)-[6-chloro-1-(2-dimethylamino-ethyl)-1H-indol-3-yl]-methanone

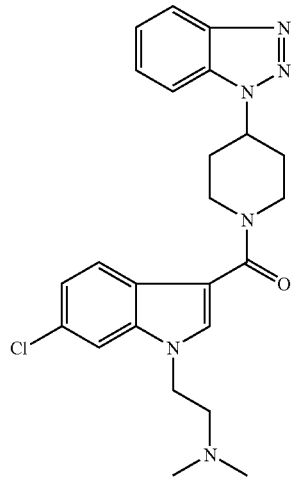

and

Example 18

(4-Benzotriazol-1-yl-piperidin-1-yl)-(7-chloro-2-methyl-1,2,3,4-tetrahydro-pyrazino[1,2-a]indol-10-yl)-methanone

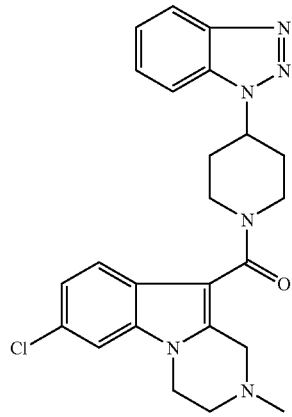

A mixture of 0.20 g (0.41 mmol) (4-benzotriazol-1-yl-piperidin-1-yl)-[6-chloro-1-(2-methylamino-ethyl)-1H-indol-3-yl]-methanone hydrochloride, 0.057 ml (0.41 mmol) triethylamine and 0.10 g (3.3 mmol) paraformaldehyde in 4 ml methanol was heated at reflux for 7 h. After cooling to 0° C. 0. were added 052 g (0.82 mmol) sodium cyanoborohydride. The cooling bath was removed and the reaction mixture was stirred at room temperature for 16 h. Quenching with 1 M aqueous sodium hydroxide solution was followed by extraction with two portions of ethyl acetate. The combined organic extracts were dried over sodium sulfate and concentrated in vacuo. Flash chromatography gave 0.040 g (22%) (4-benzotriazol-1-yl-piperidin-1-yl)-[6-chloro-1-(2-dimethylamino-ethyl)-1H-indol-3-yl]-methanone as a white solid (ES-MS m/e (%): 451 (M+H⁺, 100)) and 0.11 g (60%) (4-benzotriazol-1-yl-piperidin-1-yl)-(7-chloro-2-methyl-1,2,3,4-tetrahydro-pyrazino[1,2-a]indol-10-yl)-methanone as a white solid (ES-MS m/e (%): 449 (M+H⁺, 100)).

The invention claimed is:
1. A compound of formula (I-b)

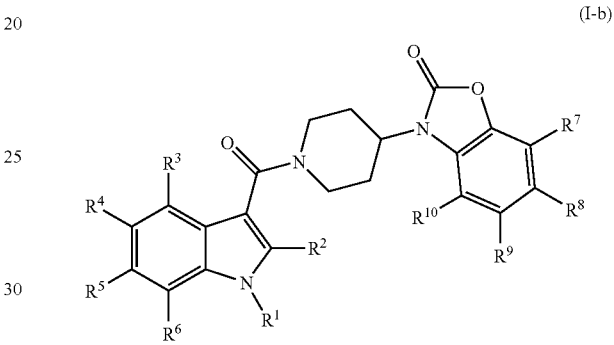

wherein
$R^1$ is H,
$C_{1-12}$-alkyl, optionally substituted with CN or OH,
$C_{1-6}$-haloalkyl,
$C_{2-12}$-alkenyl,
—$(CR^iR^{ii})_m$—$R^a$,
wherein $R^i$ and $R^{ii}$ are independently from each other H, methyl, or ethyl;
wherein m is from 0 to 4;
wherein $R^a$ is
phenyl, 5- to 6-membered heteroaryl, 3- to 7-membered heterocycloalkyl or 3 to 7-membered cylcoalkyl,
which are optionally substituted with one or more A,
or
—$NR^bR^c$, wherein $R^b$ and $R^c$ are each independently hydrogen,
hydroxy,
$C_{1-6}$-alkyl,
—$S(O)_2$—$C_{1-6}$-alkyl, or
—$C(O)$—$C_{1-6}$-alkyl,
—$(CR^{iii}R^{iv})_n$—$C(O)R^d$,
wherein $R^{iii}$ and $R^{iv}$ are independently from each other H, methyl, or ethyl;
wherein n is from 0 to 4;
wherein $R^d$ is
$C_{1-6}$-alkoxy,
—$NR^eR^f$, wherein $R^e$ and $R^f$ are each independently hydrogen,
$C_{1-6}$-alkyl, or
—$(C_{2-6}$-alkylene$)NR^gR^h$; wherein $R^g$ and $R^h$ are each independently hydrogen, $C_{1-6}$-alkyl, or
—$C(O)O$—$C_{1-6}$-alkyl, phenyl, 5- to 6-membered heteroaryl, 3- to 7-membered heterocycloalkyl or 3 to 7-membered cycloalkyl,
which are optionally substituted with one or more A,
—S(O)$_2$-phenyl, wherein phenyl is optionally substituted with one or more halo, C$_{1-6}$-haloalkyl, C$_{1-6}$-alkoxy, C$_{1-6}$-haloalkoxy, nitro, hydroxy or cyano;
—S(O)$_2$—C$_{1-6}$-alkyl,
—S(O)$_2$N(C$_{1-6}$-alkyl)$_2$,
—S(O)$_2$NH(C$_{1-6}$-alkyl);
A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$ C$_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, —(CH$_2$)$_x$—R''',
wherein x is from 0 to 4,
R' and R'' are each independently H or C$_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, C$_{1-6}$-haloalkyl, C$_{1-6}$-alkyl, or C$_{1-6}$-alkoxy,
R$^2$ is hydrogen,
C$_{1-6}$-alkyl,
—C(O)R$^n$, wherein R$^n$ is
C$_{1-6}$-alkyl,
3 to 7-membered heterocycloalkyl, optionally substituted with one, two or three C$_{1-6}$-alkyl, —C(O)O—C$_{1-6}$-alkyl, or —S(O)$_2$—C$_{1-6}$-alkyl,
NR$^j$R$^k$, wherein R$^j$ and R$^k$ are each independently hydrogen,
C$_{1-6}$-alkyl,
—(C$_{2-6}$-alkylene)-NR$^l$R$^m$; wherein R$^l$ and R$^m$ are each independently hydrogen, C$_{1-6}$-alkyl, or —C(O)O—C$_{1-6}$-alkyl; or
R$^3$, R$^4$, R$^5$, R$^6$ are each independently hydrogen, halo, C$_{1-6}$-alkyl, halo-C$_{1-6}$-alkyl, C$_{1-6}$-alkoxy or C$_{1-6}$-haloalkoxy;
R$^7$, R$^8$, R$^9$, R$^{10}$ are each independently hydrogen, halo, C$_{1-6}$-alkyl, halo-C$_{1-6}$-alkyl, C$_{1-6}$-alkoxy or C$_{1-6}$-haloalkoxy;
or a pharmaceutically acceptable salt thereof,
with the proviso that compounds wherein R$^1$, R$^2$, R$^3$, R$^4$, R$^5$ and R$^6$ are all simultaneously hydrogen are excluded.

2. A compound of claim 1, wherein
R$^1$ is H,
C$_{2-6}$-alkyl, optionally substituted with CN or OH,
C$_{1-6}$-haloalkyl,
—(CR$^i$R$^{ii}$)$_m$—R$^a$,
wherein R$^i$ and R$^{ii}$ are independently from each other H, methyl, or ethyl;
wherein m is from 0 to 4;
wherein R$^a$ is
phenyl, 5- to 6-membered heteroaryl, 3- to 7-membered heterocycloalkyl or 3 to 7-membered cycloalkyl,
which are optionally substituted with one or more A,
or
—NR$^b$R$^c$, wherein R$^b$ and R$^c$ are each independently hydrogen, C$_{1-6}$-alkyl, —S(O)$_2$—C$_{1-6}$-alkyl, or —C(O)—C$_{1-6}$-alkyl, —(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is
C$_{1-6}$-alkoxy,
—NR$^e$R$^f$, wherein R$^e$ and R$^f$ are each independently hydrogen,
C$_{1-6}$-alkyl, or
—(C$_{2-6}$-alkylene)NR$^g$R$^h$; wherein R$^g$ and R$^h$ are each independently hydrogen, C$_{1-6}$-alkyl, or —C(O)O—C$_{1-6}$-alkyl,
phenyl, 5- to 6-membered heteroaryl, 3- to 7-membered heterocycloalkyl or 3 to 7-membered cycloalkyl,
which are optionally substituted with one or more A,
—S(O)$_2$—C$_{1-6}$-alkyl,
—S(O)$_2$N(C$_{1-6}$-alkyl)$_2$,
—S(O)$_2$NH(C$_{1-6}$-alkyl);
A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$ C$_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, —(CH$_2$)$_x$—R''',
wherein x is from 0 to 4,
R' and R'' are each independently H or C$_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, C$_{1-6}$-haloalkyl, C$_{1-6}$-alkyl, or C$_{1-6}$-alkoxy.

3. The compound of claim 1, wherein
R$^1$ is H,
C$_{2-6}$-alkyl, optionally substituted with CN or OH,
C$_{1-6}$-haloalkyl,
—(CR$^i$R$^{ii}$)$_m$—R$^a$,
wherein R$^i$ and R$^{ii}$ are independently from each other H, methyl, or ethyl;
wherein m is from 1 to 4;
wherein R$^a$ is
phenyl, 5- to 6-membered heteroaryl, 3- to 7-membered heterocycloalkyl or 3 to 7-membered cycloalkyl,
which are optionally substituted with one or more A,
or
—NR$^b$R$^c$, wherein R$^b$ and R$^c$ are each independently hydrogen, C$_{1-6}$-alkyl, —S(O)$_2$—C$_{1-6}$-alkyl, or —C(O)—C$_{1-6}$-alkyl, —(CR$^{iii}$R$^{iv}$)$_n$—C(O)R$^d$,
wherein R$^{iii}$ and R$^{iv}$ are independently from each other H, methyl, or ethyl;

wherein n is from 0 to 4;
wherein $R^d$ is
- $C_{1-6}$-alkoxy,
- —$NR^eR^f$, wherein $R^e$ and $R^f$ are each independently
  - hydrogen,
  - $C_{1-6}$-alkyl, or
  - —($C_{2-6}$-alkylene)$NR^gR^h$; wherein $R^g$ and $R^h$ are each independently hydrogen, $C_{1-6}$-alkyl, or —C(O)O—$C_{1-6}$-alkyl,
- phenyl, 5- to 6-membered heteroaryl, 3- to 7-membered heterocycloalkyl or 3 to 7-membered cylcoalkyl,
  which are optionally substituted with one or more A,
- —S(O)$_2$—$C_{1-6}$-alkyl,
- —S(O)$_2$N($C_{1-6}$-alkyl)$_2$,
- —S(O)$_2$NH($C_{1-6}$-alkyl);

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}C_{1-6}$-alkyl, nitro, cyano, —($C_{1-6}$-alkylene)-O—$C_{1-6}$-alkyl, —($C_{1-6}$-alkylene)-OR''', —C(O)OC$_{1-6}$-alkyl, —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl, optionally substituted with one, two, or three halo, $C_{1-6}$-haloalkyl, $C_{1-6}$-alkyl, or $C_{1-6}$-alkoxy.

4. The compound of claim 1, wherein $R^2$ is hydrogen or $C_{1-6}$-alkyl.

5. The compound of claim 1, wherein $R^3$ and $R^6$ are hydrogen.

6. The compound of claim 1, wherein $R^1$ is hydrogen.

7. The compound of claim 1, wherein $R^1$ is $C_{1-12}$-alkyl, optionally substituted with CN or OH.

8. The compound of claim 1, wherein $R^1$ is $C_{1-6}$-haloalkyl or $C_{2-12}$-alkenyl.

9. The compound of claim 1, wherein $R^1$ is —S(O)$_2$-phenyl, wherein phenyl is optionally substituted with one or more halo, $C_{1-6}$-haloalkyl, $C_{1-6}$-alkyl, $C_{1-6}$-alkoxy, $C_{1-6}$-haloalkoxy, nitro, hydroxy or cyano.

10. The compound of claim 1, wherein $R^1$ is —S(O)$_2$—$C_{1-6}$- alkyl, —S(O)$_2$N($C_{1-6}$-alkyl)$_2$, or —S(O)$_2$NH($C_{1-6}$-alkyl).

11. The compound of claim 1, wherein A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, $C_{1-6}$-thioalkyl, —S(O)$_2$—$C_{1-6}$- alkyl, cyano, —CH$_2$OCH$_3$, —C(O)O—$C_{1-6}$-alkyl, —C(O)NR'R'', —S(O)$_2$NR'R'', —NR'C(O)—$C_{1-6}$-alkyl, —NR'S(O)$_2$—$C_{1-6}$-alkyl, benzyl, or phenyl
wherein R' and R'' are each independently H or $C_{1-6}$-alkyl.

12. The compound of claim 1, wherein $R^3$, $R^4$, $R^5$, and $R^6$ are each independently hydrogen, halo, $C_{1-6}$-alkyl, $C_{1-6}$-haloalkyl, $C_{1-6}$-alkoxy, or $C_{1-6}$-haloalkoxy.

13. The compound of claim 1, wherein $R^4$ is hydrogen, Cl, F, or methyl.

14. The compound of claim 1, wherein $R^5$ is hydrogen, halo, CF$_3$, methoxy, or —OCF$_3$.

15. The compound of claim 1, wherein $R^3$ and $R^6$ are hydrogen, $R^4$ is hydrogen, F, Cl or methyl, and $R^5$ is halo, CF$_3$, methoxy or OCF$_3$.

16. The compound of claim 1, wherein $R^7$, $R^8$, $R^9$, and $R^{10}$ are each independently hydrogen, halo, $C_{1-6}$-alkyl, halo-$C_{1-6}$-alkyl, $C_{1-6}$-alkoxy, or $C_{1-6}$-haloalkoxy.

17. The compound of claim 1, selected from the group consisting of 3-[1-(6-Chloro-1H-indole-3-carbonyl)-piperidin-4-yl]-3H-benzooxazol-2-one, and 2-{6-Chloro-3-[4-(2-oxo-benzooxazol-3-yl)-piperidine-1-carbonyl]-indol-1-yl}-N-methyl-acetamide.

18. A pharmaceutical composition comprising a therapeutically effective amount of a compound of formula I-b

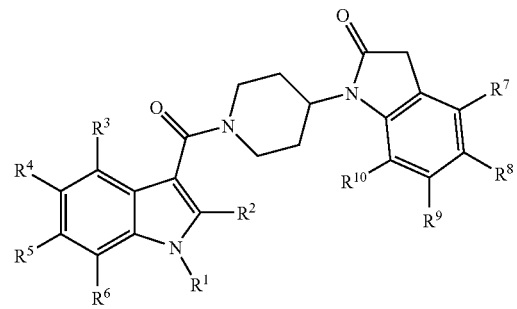

(I-b)

wherein
$R^1$ is H,
$C_{1-12}$-alkyl, optionally substituted with CN or OH,
$C_{1-6}$-haloalkyl,
$C_{2-12}$-alkenyl,
—(CR$^i$R$^{ii}$)$_m$—$R^a$,
  wherein R' and R'' are independently from each other H, methyl, or ethyl;
  wherein m is from 0 to 4;
  wherein $R^a$ is
    phenyl, 5- to 6-membered heteroaryl, 3- to 7-membered heterocycloalkyl or 3 to 7-membered cylcoalkyl,
    which are optionally substituted with one or more A,
or
—NR$^b$R$^c$, wherein R$^b$ and R$^c$ are each independently
  hydrogen,
  hydroxy,
  —S(O)$_2$—$C_{1-6}$-alkyl, or
  —C(O)—$C_{1-6}$-alkyl,
—(CR$^{iii}$R$^{iv}$)$_n$—C(O)$R^d$,
  wherein R$^{iii}$ and R$^{iv}$ are independently from each other H, methyl, or ethyl;
  wherein n is from 0 to 4;
  wherein $R^d$ is
    $C_{1-6}$-alkoxy,
    —NR$^e$R$^f$, wherein R$^e$ and R$^f$ are each independently
      hydrogen,
      $C_{1-6}$-alkyl, or
      —($C_{2-6}$-alkylene)NR$^g$R$^h$; wherein R$^g$ and R$^h$ are each independently hydrogen, $C_{1-6}$-alkyl, or —C(O)O—$C_{1-6}$-alkyl,
    phenyl, 5- to 6-membered heteroaryl, 3- to 7-membered heterocycloalkyl or 3 to 7-membered cycloalkyl,
      which are optionally substituted with one or more A,
—S(O)$_2$-phenyl, wherein phenyl is optionally substituted with one or more halo, $C_{1-6}$-haloalkyl, $C_{1-6}$-alkoxy, $C_{1-6}$-haloalkoxy, nitro, hydroxy or cyano;

—S(O)$_2$—C$_{1-6}$-alkyl,
—S(O)$_2$N(C$_{1-6}$-alkyl)$_2$,
—S(O)$_2$NH(C$_{1-6}$-alkyl);

A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$ C$_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, —(CH$_2$)$_x$—R''', wherein x is from 0 to 4, R' and R'' are each independently H or C$_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, C$_{1-6}$-haloalkyl, C$_{1-6}$-alkyl, or C$_{1-6}$-alkoxy, R$^2$ is hydrogen,
C$_{1-6}$-alkyl,
—C(O)R'', wherein R'' is
C$_{1-6}$-alkyl,
3 to 7-membered heterocycloalkyl, optionally substituted with one, two or three C$_{1-6}$-alkyl, —C(O)O—C$_{1-6}$-alkyl, or —S(O)$_2$—C$_{1-6}$-alkyl,
NR$^j$R$^k$, wherein R$^j$ and R$^k$ are each independently hydrogen,
C$_{1-6}$-alkyl,
—(C$_{2-6}$-alkylene)-NR$^l$R$^m$; wherein R$^l$ and R$^m$ are each independently hydrogen, C$_{1-6}$-alkyl, or —C(O)O—C$_{1-6}$-alkyl; or R$^3$, R$^4$, R$^5$, R$^6$ are each independently hydrogen, halo, C$_{1-6}$-alkyl, halo-C$_{1-6}$-alkyl, C$_{1-6}$-alkoxy or C$_{1-6}$-haloalkoxy;

R$^7$, R$^8$, R$^9$, R$^{10}$ are each independently hydrogen, halo, C$_{1-6}$-alkyl, halo-C$_{1-6}$-alkyl, C$_{1-6}$-alkoxy or C$_{1-6}$-haloalkoxy;

or a pharmaceutically acceptable salt thereof, with the proviso that compounds wherein R$^1$, R$^2$, R$^3$, R$^4$, R$^5$ and R$^6$ are all simultaneously hydrogen are excluded.

* * * * *